(12) United States Patent
Friess et al.

(10) Patent No.: US 7,342,030 B2
(45) Date of Patent: Mar. 11, 2008

(54) INDOLE DERIVATIVES

(75) Inventors: Thomas Friess, Diessen-Dettenhofen (DE); Ulrike Reiff, Penzberg (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 273 days.

(21) Appl. No.: 11/230,356

(22) Filed: Sep. 20, 2005

(65) Prior Publication Data

US 2006/0063812 A1    Mar. 23, 2006

(30) Foreign Application Priority Data

Sep. 22, 2004  (EP)  .................................. 04022475

(51) Int. Cl.
*A61K 31/427*   (2006.01)
*C07D 417/02*   (2006.01)
*C07D 403/14*   (2006.01)

(52) U.S. Cl. ...................... 514/359; 548/181; 548/215; 548/255

(58) Field of Classification Search ................ 514/359; 548/181, 215, 255
See application file for complete search history.

(56) References Cited

FOREIGN PATENT DOCUMENTS

| EP | 1270571 | 1/2003 |
|----|---------|--------|
| WO | WO 98/03505 | 1/1998 |
| WO | WO 01/77107 | 10/2001 |
| WO | WO 03/031442 | 4/2003 |
| WO | WO 03/059907 | 7/2003 |

OTHER PUBLICATIONS

Wilks, A.F., Progress in Growth Factor Research, 2, pp. 97-111 (1990).
Chan et al., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ransom et al., Oncology, 63 (Suppl. 1), pp. 17-24 (2002).
Bastin et al., Organic Proc. Res. Dev., 4, pp. 427-435 (2000).

*Primary Examiner*—Kamal A. Saeed
*Assistant Examiner*—Robert Havlin
(74) *Attorney, Agent, or Firm*—George W. Johnston; Patricia S. Rocha-Tramaloni; Gene J. Yao

(57) ABSTRACT

The present invention relates to the compounds of formula I:

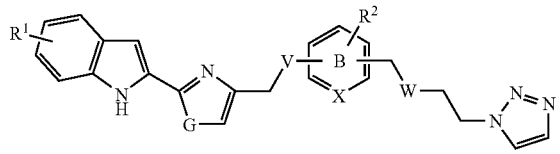

formula I, their pharmaceutically acceptable salts, enantiomeric forms, diastereoisomers and racemates, the preparation of the above-mentioned compounds, compositions containing such compounds and their manufacture, as well as the use of such compounds in the control or prevention of illnesses such as cancer.

16 Claims, No Drawings

INDOLE DERIVATIVES

PRIORITY TO RELATED APPLICATIONS

This application claims the benefit of European Application No. 04022475.0, filed Sep. 22, 2004, which is hereby incorporated by reference in its entirety.

FIELD OF THE INVENTION

The present invention relates to novel indole derivatives, to a process for their manufacture, pharmaceutical compositions containing them and their manufacture as well as the use of these compounds as pharmaceutically active agents.

BACKGROUND OF THE INVENTION

Protein tyrosine kinases (PTKs) catalyze the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394-401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443-478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer (colon, rectal or stomach cancer), leukemia and ovarian, bronchial and pancreatic cancer. High levels of these receptors correlate with poor prognosis and response to treatment (Wright, C., et al., Br. J. Cancer 65 (1992) 118-121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6-16; Ranson, M., and Sliwkowski, M. X., Oncology 63 (suppl. 1) (2002) 17-24).

Some substituted oxazoles are known in the art. WO 98/03505, EP 1 270 571, WO 01/77107, WO 03/031442 and WO 03/059907 disclose related heterocyclic compounds as -tyrosine kinase inhibitors.

However there remains a need for new compounds with improved therapeutic properties, such as enhanced activity, decreased toxicity, better solubility and improved pharmacokinetic profile, to name only a few.

SUMMARY OF THE INVENTION

The present invention relates to compounds of the general formula I and pharmaceutically acceptable salts thereof wherein formula I is:

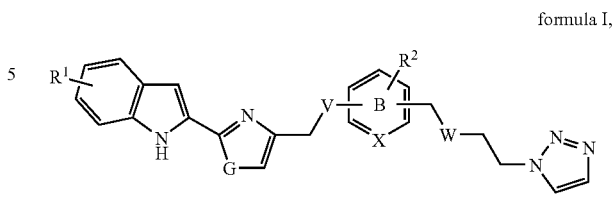

formula I, wherein:
R$^1$ is selected from the group consisting of:
  (a) hydrogen,
  (b) halogen,
  (c) —O-alkyl, wherein the alkyl group is optionally substituted with one or more halogens,
  (d) —S-alkyl, wherein the alkyl group is optionally substituted with one or more halogens, and
  (e) alkyl, wherein the alkyl is optionally substituted with one or more halogens;
R$^2$ is selected from the group consisting of:
  (a) hydrogen,
  (b) halogen,
  (c) alkyl, wherein the alkyl is optionally substituted with one or more halogens, and
  (d) —O-alkyl, wherein the alkyl group is optionally substituted with one or more halogens;
G is selected from the group consisting of: —O— and —S—;
V is selected from the group consisting of: —O—, —NH—, —S—, —S(O)—, and —S(O)$_2$—;
W is selected from the group consisting of: a single bond, —CH$_2$—, —O—, —S—, —S(O)— and —S(O)$_2$—;
X is selected from the group consisting of: =CH— and =N—; and ring B is selected from the group consisting of:
  (a) 1,4-phenylene,
  (b) 1,3-phenylene,
  (c) 2,5-pyridindiyl, and
  (d) 3,6-pyridindiyl.

The compounds of formula I are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signaling pathway and therefore possess anti-proliferative activity. The present invention provides the compounds of formula I and their pharmaceutically acceptable salts, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above like common human cancers (e.g. breast cancer, gastrointestinal cancer (colon, rectal or stomach cancer), leukemia and ovarian, bronchial and pancreatic cancer) or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 4, preferably 1 or 2, carbon atoms. Examples are methyl, ethyl, n-propyl, isopropyl, n-butyl, 2-butyl, and t-butyl. If said alkyl group is substituted one or several times by halogen, it is substituted preferably by fluorine. Examples are difluoromethyl, trifluoromethyl, 2,2,2-trifluoroethyl, perfluorethyl and the like.

As used herein, the term "halogen" means fluorine, chlorine, bromine or iodine, preferably fluorine, chlorine or bromine and more preferably fluorine or chlorine.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, in relation to mass spectrometry (MS) the term "ESI+" refers to positive electrospray ionization mode and the terms "API+" and "API−" refer to positive and negative atmospheric pressure ionization mode.

As used herein, the term "CDCl3" refers to deuterated chloroform.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

Preferred are the pharmaceutically acceptable salts, which are formed with p-toluenesulfonic acid, naphthalenesulfonic acid, naphthalenedisulfonic acid, methanesulfonic acid and hydrochloric acid.

In a preferred embodiment, $R^1$ of formula I represents trifluoromethoxy, chloro or fluoro.

In another preferred embodiment, the position of $R^2$ of formula I on the central phenyl ring is meta to the position of V.

An embodiment are the compounds of formula I, wherein V is —O—, —NH— or —S(O)$_2$—.

Another embodiment are the compounds of formula I, wherein V is —O— or —S(O)$_2$—.

Another embodiment are the compounds of formula I, wherein V is —O—.

Another embodiment are the compounds of formula I, wherein:
  $R^1$ is selected from the group consisting of:
    (a) hydrogen;
    (b) halogen;
    (c) —O-alkyl; wherein the alkyl group is optionally substituted one or more times by fluorine;
    (d) —S-alkyl; wherein the alkyl group is optionally substituted one or more times by fluorine; and
    (e) alkyl; wherein the alkyl is optionally substituted one or more times by fluorine;
  $R^2$ is selected from the group consisting of hydrogen, halogen and alkyl;
  V is —O—;
  W is selected from the group consisting of a single bond, —CH$_2$—, —O—, —S(O)— and —S(O)$_2$—;
  X is =CH—; and
  ring B is selected from the group consisting of 1,4-phenylene and 1,3-phenylene.

Another embodiment are the compounds of formula I, wherein:
  $R^1$ is selected from the group consisting of:
    (a) hydrogen,
    (b) halogen,
    (c) —O-alkyl, wherein the alkyl group is optionally substituted one or more times by fluorine;
    (d) —S-alkyl, wherein the alkyl group is optionally substituted one or more times by fluorine; and
    (e) alkyl; wherein the alkyl is optionally substituted one or more times by fluorine;
  $R^2$ is selected from the group consisting of hydrogen, halogen and alkyl;
  V is —O—;
  W is selected from the group consisting of a single bond, —CH$_2$—, —O— and —S(O)—;
  X is =CH—; and
  ring B is selected from the group consisting of 1,4-phenylene and 1,3-phenylene.

Another embodiment are the compounds of formula I, wherein:
  $R^1$ is selected from the group consisting of:
    (a) hydrogen,
    (b) halogen, and
    (c) —O-alkyl; wherein the alkyl group is optionally substituted one or more times by fluorine;

G is —O—;
V is —O—;
W is —CH₂—;
X is =CH—; and
ring B is 1,4-phenylene.

For example, such compounds can be selected from the group consisting of:
5-Chloro-2-{4-[4-(4-[1,2,3]triazol-1-yl-butyl)-phenoxymethyl]-oxazol-2-yl}-1H-indole;
5-Fluoro-2-{4-[4-(4-[1,2,3]triazol-1-yl-butyl)-phenoxymethyl]-oxazol-2-yl}-1H-indole;
6-Fluoro-2-{4-[4-(4-[1,2,3]triazol-1-yl-butyl)-phenoxymethyl]-oxazol-2-yl}-1H-indole;
2-{4-[4-(4-[1,2,3]Triazol-1-yl-butyl)-phenoxymethyl]-oxazol-2-yl}-5-trifluoromethoxy-1H-indole; and
6-Chloro-2-{4-[4-(4-[1,2,3]triazol-1-yl-butyl)-phenoxymethyl]-oxazol-2-yl}-1H-indole.

Another embodiment are the compounds of formula I, wherein:
R¹ is selected from the group consisting of:
  (a) hydrogen,
  (b) halogen, and
  (c) —O-alkyl; wherein the alkyl group is optionally substituted one or more times by fluorine;
R² is alkyl;
G is —O—;
V is —O—;
W is —CH₂—;
X is =CH—; and
ring B is 1,4-phenylene.

For example, such compounds can be selected from the group consisting of:
5-Fluoro-2-{4-[3-methyl-4-(4-[1,2,3]triazol-1-yl-butyl)-phenoxymethyl]-oxazol-2-yl}-1H-indole;
2-{4-[3-Methyl-4-(4-[1,2,3]triazol-1-yl-butyl)-phenoxymethyl]-oxazol-2-yl}-5-trifluoromethoxy-1H-indole;
6-Fluoro-2-{4-[3-methyl-4-(4-[1,2,3]triazol-1-yl-butyl)-phenoxymethyl]-oxazol-2-yl}-1H-indole; and
6-Chloro-2-{4-[3-methyl-4-(4-[1,2,3]triazol-1-yl-butyl)-phenoxymethyl]-oxazol-2-yl}-1H-indole.

Another embodiment are the compounds of formula I, wherein:
R¹ is selected from the group consisting of:
  (a) hydrogen,
  (b) halogen, and
  (c) —O-alkyl; wherein the alkyl group is optionally substituted one or more times by fluorine;
R² is selected from the group consisting of hydrogen and alkyl;
G is —O—;
V is —O—;
W is selected from the group consisting of —O—, —S(O)— and —S(O)₂—;
X is =CH—; and
ring B is 1,4-phenylene.

For example, such compounds can be selected from the group consisting of:
5-Chloro-2-{4-[4-(2-[1,2,3]triazol-1-yl-ethoxymethyl)-phenoxymethyl]-oxazol-2-yl}-1H-indole;
5-Fluoro-2-{4-[4-(2-[1,2,3]triazol-1-yl-ethoxymethyl)-phenoxymethyl]-oxazol-2-yl}-1H-indole;
5-Chloro-2-{4-[4-(2-[1,2,3]triazol-1-yl-ethanesulfinylmethyl)-phenoxymethyl]-oxazol-2-yl}-1H-indole;
5-Chloro-2-{4-[4-(2-[1,2,3]triazol-1-yl-ethanesulfinylmethyl)-phenoxymethyl]-oxazol-2-yl}-1H-indole;
5-Fluoro-2-{4-[3-methyl-4-(2-[1,2,3]triazol-1-yl-ethoxymethyl)-phenoxymethyl]-oxazol-2-yl}-1H-indole;
5-Fluoro-2-{4-[3-methyl-4-(2-[1,2,3]triazol-1-yl-ethanesulfinylmethyl)-phenoxymethyl]-oxazol-2-yl}-1H-indole; and
5-Fluoro-2-{4-[3-methyl-4-(2-[1,2,3]triazol-1-yl-ethanesulfonylmethyl)-phenoxymethyl]-oxazol-2-yl}-1H-indole.

Another embodiment are the compounds of formula I, wherein:
R¹ is selected from the group consisting of:
  (a) hydrogen,
  (b) halogen, and
  (c) —O-alkyl; wherein the alkyl group is optionally substituted one or more times by fluorine;
R² is selected from the group consisting of hydrogen and alkyl;
G is —O—;
V is —O—;
W is selected from the group consisting of —O— and —S(O)—;
X is =CH—; and
ring B is 1,4-phenylene.

Another embodiment are the compounds of formula I, wherein:
R¹ is selected from the group consisting of:
  (a) hydrogen,
  (b) halogen, and
  (c) —O-alkyl; wherein the alkyl group is optionally substituted one or more times by fluorine;
R² is hydrogen;
G is —O—;
V is —O—;
W is a single bond;
X is =CH—; and
ring B is 1,3-phenylene.

For example, such compounds can be selected from the group consisting of:
5-Fluoro-2-{4-[3-(3-[1,2,3]triazol-1-yl-propyl)-phenoxymethyl]-oxazol-2-yl}-1H-indole;
6-Chloro-2-{4-[3-(3-[1,2,3]triazol-1-yl-propyl)-phenoxymethyl]-oxazol-2-yl}-1H-indole; and
2-{4-[3-(3-[1,2,3]Triazol-1-yl-propyl)-phenoxymethyl]-oxazol-2-yl}-5-trifluoromethoxy-1H-indole.

Another embodiment are the compounds of formula I, wherein:
R¹ is selected from the group consisting of:
  (a) hydrogen,
  (b) halogen, and
  (c) —O-alkyl; wherein the alkyl group is optionally substituted one or more times by fluorine;
R² is hydrogen;
G is —S—;
V is —O—;
W is selected from the group consisting of: —CH₂—, —O— and —S(O)—;
X is =CH—; and
ring B is 1,4-phenylene.

For example, such compounds can be selected from the group consisting of:
5-Chloro-2-{4-[4-(4-[1,2,3]triazol-1-yl-butyl)-phenoxymethyl]-thiazol-2-yl}-1H-indole;
5-Chloro-2-{4-[4-(2-[1,2,3]triazol-1-yl-ethoxymethyl)-phenoxymethyl]-thiazol-2-yl}-1H-indole; and
5-Chloro-2-{4-[4-(2-[1,2,3]triazol-1-yl-ethanesulfinylmethyl)-phenoxymethyl]-thiazol-2-yl}-1H-indole.

Still another embodiment are the compounds of formula I, wherein V is —S(O)₂—.

Yet another embodiment are the compounds of formula I, wherein:
R$^1$ is selected from the group consisting of:
(a) hydrogen,
(b) halogen, and
(c) —O-alkyl; wherein the alkyl group is optionally substituted one or more times by fluorine;
R$^2$ is hydrogen;
G is —O—;
V is —S(O)$_2$—;
W is —CH$_2$—;
X is =CH—; and
ring B is 1,4-phenylene.

For example, such compounds can be selected from the group consisting of:
5-Fluoro-2-{4-[4-(4-[1,2,3]triazol-1-yl-butyl)-benzenesulfonylmethyl]-oxazol-2-yl}-1H-indole; and
2-{4-[4-(4-[1,2,3]Triazol-1-yl-butyl)-benzenesulfonylmethyl]-oxazol-2-yl}-5-trifluoromethoxy-1H-indole.

Another embodiment are the compounds of formula I, wherein V is —O— or —NH—.

Still another embodiment are the compounds of formula I, wherein V is —NH—.

Still another embodiment are the compounds of formula I, wherein:
R$^1$ is selected from the group consisting of:
(a) hydrogen,
(b) halogen,
(c) —O-alkyl, wherein the alkyl group is optionally substituted one or more times by fluorine;
(d) —S-alkyl, wherein the alkyl group is optionally substituted one or more times by fluorine; and
(e) alkyl; wherein the alkyl is optionally substituted one or more times by fluorine;
R$^2$ is selected from the group consisting of:
(a) hydrogen,
(b) halogen, and
(c) alkyl; wherein the alkyl is optionally substituted one or more times by fluorine;
G is —O—;
V is —NH—;
W is a single bond or —CH$_2$. and
X is =CH— or =N—.

Yet another embodiment are the compounds of formula I, wherein:
R$^1$ is selected from the group consisting of:
(a) hydrogen,
(b) halogen, and
(c) —O-alkyl; wherein the alkyl group is optionally substituted one or more times by fluorine;
R$^2$ is hydrogen;
G is —O—;
V is —NH—;
W is —CH$_2$—;
X is =CH—; and
ring B is 1,4-phenylene.

For example, such compounds can be selected from the group consisting of:
[2-(6-Fluoro-1H-indol-2-yl)-oxazol-4-ylmethyl]-[4-(4-[1,2,3]triazol-1-yl-butyl)-phenyl]-amine;
[2-(5-Fluoro-1H-indol-2-yl)-oxazol-4-ylmethyl]-[4-(4-[1,2,3]triazol-1-yl-butyl)-phenyl]-amine;
[4-(4-[1,2,3]Triazol-1-yl-butyl)-phenyl]-[2-(5-trifluoromethoxy-1H-indol-2-yl)-oxazol-4-ylmethyl]-amine;
[2-(6-Chloro-1H-indol-2-yl)-oxazol-4-ylmethyl]-[4-(4-[1,2,3]triazol-1-yl-butyl)-phenyl]-amine; and
[2-(5-Chloro-1H-indol-2-yl)-oxazol-4-ylmethyl]-[4-(4-[1,2,3]triazol-1-yl-butyl)-phenyl]-amine.

Another embodiment are the compounds of formula I, wherein:
R$^1$ is selected from the group consisting of:
(a) hydrogen,
(b) halogen, and
(c) —O-alkyl; wherein the alkyl group is optionally substituted one or more times by fluorine;
R$^2$ is selected from the group consisting of:
(a) halogen, and
(b) alkyl; wherein the alkyl is optionally substituted one or more times by fluorine;
G is —O—;
V is —NH—;
W is —CH$_2$—;
X is =CH—; and
ring B is 1,4-phenylene.

For example, such compounds can be selected from the group consisting of:
[2-(5-Fluoro-1H-indol-2-yl)-oxazol-4-ylmethyl]-[3-methyl-4-(4-[1,2,3]triazol-1-yl-butyl)-phenyl]-amine;
[2-(6-Fluoro-1H-indol-2-yl)-oxazol-4-ylmethyl]-[3-methyl-4-(4-[1,2,3]triazol-1-yl-butyl)-phenyl]-amine;
[2-(5-Chloro-1H-indol-2-yl)-oxazol-4-ylmethyl]-[3-methyl-4-(4-[1,2,3]triazol-1-yl-butyl)-phenyl]-amine;
[2-(5-Chloro-1H-indol-2-yl)-oxazol-4-ylmethyl]-[4-(4-[1,2,3]triazol-1-yl-butyl)-3-trifluoromethyl-phenyl]-amine;
[2-(5-Fluoro-1H-indol-2-yl)-oxazol-4-ylmethyl]-[4-(4-[1,2,3]triazol-1-yl-butyl)-3-trifluoromethyl-phenyl]-amine;
[2-(5-Fluoro-1H-indol-2-yl)-oxazol-4-ylmethyl]-[3-fluoro-4-(4-[1,2,3]triazol-1-yl-butyl)-phenyl]-amine;
[2-(5-Chloro-1H-indol-2-yl)-oxazol-4-ylmethyl]-[3-fluoro-4-(4-[1,2,3]triazol-1-yl-butyl)-phenyl]-amine;
[2-(5-Fluoro-1H-indol-2-yl)-oxazol-4-ylmethyl]-[2-fluoro-4-(4-[1,2,3]triazol-1-yl-butyl)-phenyl]-amine; and
[2-(5-Chloro-1H-indol-2-yl)-oxazol-4-ylmethyl]-[2-fluoro-4-(4-[1,2,3]triazol-1-yl-butyl)-phenyl]-amine.

Still another embodiment are the compounds of formula I, wherein:
R$^1$ is selected from the group consisting of:
(a) hydrogen,
(b) halogen, and
(c) —O-alkyl; wherein the alkyl group is optionally substituted one or more times by fluorine;
R$^2$ is hydrogen;
G is —O—;
V is —NH—;
W is a single bond;
X is =CH—; and
ring B is 1,3-phenylene.

For example, such compounds can be selected from the group consisting of:
[2-(6-Chloro-1H-indol-2-yl)-oxazol-4-ylmethyl]-[3-(3-[1,2,3]triazol-1-yl-propyl)-phenyl]-amine; and
[2-(5-Fluoro-1H-indol-2-yl)-oxazol-4-ylmethyl]-[3-(3-[1,2,3]triazol-1-yl-propyl)-phenyl]-amine.

Still another embodiment are the compounds of formula I, wherein:
R$^1$ is selected from the group consisting of:
(a) hydrogen,
(b) halogen, and
(c) —O-alkyl; wherein the alkyl group is optionally substituted one or more times by fluorine;
R$^2$ is hydrogen;
G is —O—;
V is —NH—;

W is —CH$_2$—;
X is =N—; and
ring B is selected from the group consisting of 2,5-pyridindiyl and 3,6-pyridindiyl.

For example, such compounds can be selected from the group consisting of:

[2-(5-Fluoro-1H-indol-2-yl)-oxazol-4-ylmethyl]-[6-(4-[1,2,3]triazol-1-yl-butyl)-pyridin-3-yl]-amine; and

[2-(5-Fluoro-1H-indol-2-yl)-oxazol-4-ylmethyl]-[5-(4-[1,2,3]triazol-1-yl-butyl)-pyridin-2-yl]-amine.

Another embodiment are the compounds of formula I, wherein:
R$^1$ is selected from the group consisting of:
 (a) halogen,
 (b) —O-alkyl, wherein the alkyl group is optionally substituted one to three times by fluorine; and
 (c) alkyl; wherein the alkyl is optionally substituted one to three times by fluorine;
R$^2$ is selected from the group consisting of:
 (a) hydrogen,
 (b) halogen, and
 (c) alkyl; wherein the alkyl is optionally substituted one to three times by fluorine;
V is selected from the group consisting of —O—, —NH— and —S(O)$_2$—; and
W is selected from the group consisting of a single bond, —CH$_2$—, —O—, —S(O)— and —S(O)$_2$—.

Another embodiment are the compounds of formula I, wherein:
R$^1$ is selected from the group consisting of:
 (a) halogen, and
 (b) —O-alkyl; the alkyl group being substituted one to three times by fluorine;
R$^2$ is selected from the group consisting of:
 (a) hydrogen,
 (b) halogen, and
 (c) alkyl; the alkyl being optionally substituted one to three times by fluorine;
V is selected from the group consisting of —O—, —NH— and —S(O)$_2$—; and
W is selected from the group consisting of a single bond, —CH$_2$—, —O—, —S(O)— and —S(O)$_2$—.

Still another embodiment of the invention is a process for the manufacture of the compounds of formula I, wherein:
(a) the compound of formula VI:

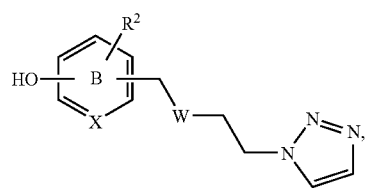

formula VI wherein W, X, R$^2$ and ring B have the significance as given in formula I above, is reacted with a compound of formula V:

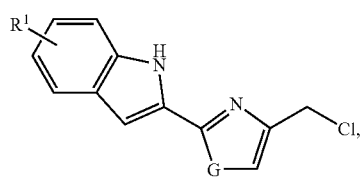

formula V wherein R$^1$ and G have the significance given above for formula I, to give the respective compound of formula Ia:

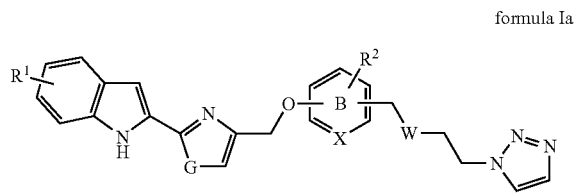

formula Ia wherein R$^1$, R$^2$, W, X, G and ring B have the significance given above for formula I and V is —O—;

(b) optionally, said compound of formula Ia is isolated from the reaction mixture, and (c) optionally, said compound of formula Ia is converted into a pharmaceutically acceptable salt.

Still another embodiment of the invention is a process for the manufacture of the compounds of formula I, wherein:
(a) the compound of formula XIII:

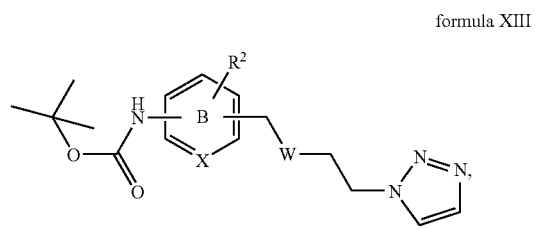

formula XIII wherein R$^2$, W, X and ring B have the significance as given in formula I above, is reacted first with a compound of formula V:

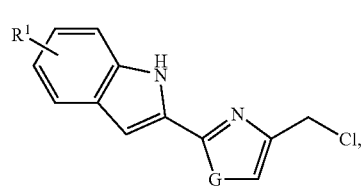

formula V wherein R$^1$ and G have the significance given above for formula I, to give the respective compound of formula XIV,

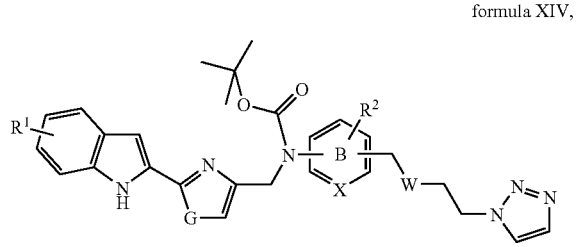

formula XIV, wherein R$^1$, R$^2$, W, X, G and ring B have the significance given above for formula I;

(b) the BOC-protecting group of said compound of formula XIV is cleaved to give the respective compound of formula Ib:

formula Ib,

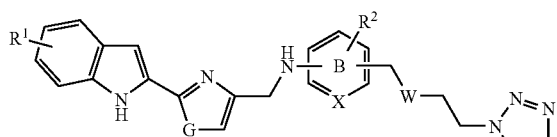

wherein $R^1$, $R^2$, W, X, G and ring B have the significance given above for formula I and V is —NH—;

(c) optionally, said compound of formula Ib is isolated from the reaction mixture, and (d) optionally, converted into a pharmaceutically acceptable salt.

The derivatives of the general formula I or a pharmaceutically acceptable salt thereof, may be prepared by any process known to be applicable for the preparation of chemically-related compounds by the one skilled in the art. Such processes, when used to prepare the indole derivatives of formula I, or a pharmaceutically-acceptable salt thereof, are provided as a further feature of the invention and are illustrated by the following representative examples of scheme 1 to 3, in which, unless otherwise stated $R^1$, $R^2$, G, V, W and X have the significance given herein before. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Scheme 1

The manufacture of the compounds of formula I varies according to the nature of "V" in formula I. The compounds of the present invention wherein "V" is —O— can be prepared according to scheme 1, and are named Ia.

Scheme 1

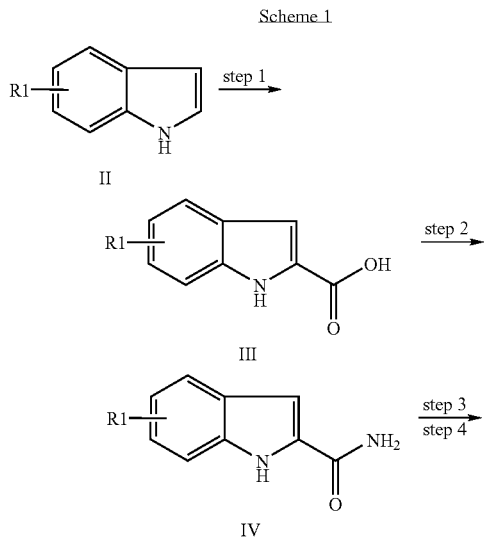

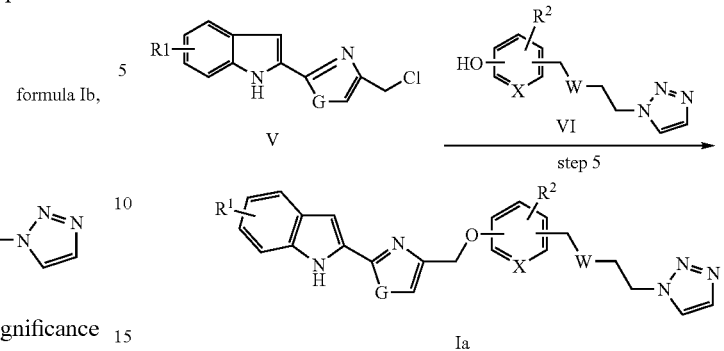

Ia

In scheme 1, G, W, X, $R^1$ and $R^2$ have the significance as given above for formula I. A method for the synthesis of the compounds of formula Ia starts from the indoles of formula II. Step 1 of the reaction sequence (scheme 1) is the carboxylation of indoles of formula II in the 2-position, using methods well known to someone skilled in the art. For this purpose indoles are e.g. first N-carboxylated by treatment with n-butyllithium and carbon dioxide and then subsequently carboxylated at the 2-position by treatment with tert-butyllithium and carbon dioxide. Aqueous workup yields the corresponding carboxylic acids of formula II. Such reactions are typically carried out in solvents like tetrahydrofuran (THF) or n-hexanes at temperatures between −78° C. and 30° C.

In step 2, scheme 1 the obtained compounds of formula III are converted into their corresponding amides of formula IV, using methods well known to someone skilled in the art, e.g. by activating the carboxylic group in said compounds of formula III with oxalyl chloride or other activating reagents in solvents like THF, dichloromethane, N,N-dimethylformamide (DMF) and mixtures thereof at temperatures varying from −30° C. to 40° C. The addition of aqueous ammonia yields the amides of formula IV.

In order to obtain the compounds of formula Ia wherein "G" is sulfur, the carboxamides of formula IV need to be converted into the corresponding thioamides, e.g. by reaction with phosphorous pentasulfide in a solvent like THF or dioxane, preferably at reflux temperature (step 3). On the other hand, in order to obtain the compounds of formula Ia wherein "G" is oxygen, this reaction step is omitted and the compounds of formula IV are immediately reacted with 1,3-dichloro-propan-2-one (step 4) to give the corresponding chlorides of formula V.

With step 4, scheme 1 the chlorides of formula V are synthesized using commonly known methods. The amides of formula IV and 1,3-dichloroacetone are subjected to a condensation/dehydration sequence yielding the compounds of formula V. Typical solvents for reactions of this kind are toluene, benzene, DMF, acetone and chloroform. If desired the reaction can be carried out under solvent free conditions. The reaction temperatures may vary from 50° C. to 150° C.

The derivatives of formula Ia can be obtained by reactions well known to someone skilled in the art, e.g. by alkylation of compounds of formula VI with compounds of formula V according to step 5 scheme 1. The alkylation can be carried out in the presence of potassium iodide or sodium iodide in solvents like DMF, methanol, ethanol, isopropanol and 2-butanone. Typical bases for this reaction are sodium methylate, sodium hydride, lithium diisopropyl amide or cesium carbonate. The reaction temperatures may vary from 50° C. to 150° C.

The phenolic intermediates of formula VI, wherein W is —O—, —S—, —S(O)— or —S(O)$_2$, may be prepared by reaction of a compound of formula VII with a compound of formula VIII:

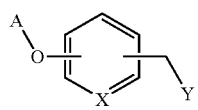

formula VII

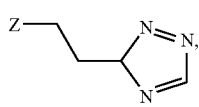

formula VIII wherein:
A denotes a suitable protecting group as defined below,
Y denotes a thiol group and
Z denotes a suitable leaving group as defined below, optional oxidation of the obtained thioether to yield a sulfoxide or a sulfone, and subsequent removal of the protecting group A; or alternatively:
A denotes a suitable protecting group as defined below, and
one of Y or Z denotes a hydroxy group,
while the other denotes a suitable leaving group E as defined below, and subsequent removal of the protecting group A.

The corresponding aniline derivatives, wherein the hydroxy group on the phenyl is replaced by an amino group, can be prepared analogously from the corresponding nitrophenyl compounds with subsequent reduction, e.g. by catalytic hydrogenation with hydrogen/Palladium, to the aniline derivative.

Reactions of compounds of formula VII with compounds of formula VIII are well known in the art. Typically, such alkylation reaction may be carried out in solvents like dimethylformamide (DMF), methanol, ethanol and isopropanol. Typical bases for this reaction are alkaline carbonates, sodium methylate, sodium hydride or lithium diisopropyl amide. The reaction temperatures may vary from 20° C. to 150° C. Other preferred alkylation procedures make use of alkaline carbonates as bases in solvents like ketones, for example cesium carbonate in butanone at reflux temperature, or sodium hydride in DMF at room temperature. Suitable leaving groups Y are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

The hydroxy protecting group A as mentioned herein is a conventional protecting group as known by the skilled artisan. Examples are tert-butoxycarbonyl (boc), propen-3-yl (allyl), triphenylmethyl (trityl) and silyl groups, e.g. tert.-butyl-dimethyl-silyl, triisopropyl-silyl.

Removal of a protecting group on a hetero atom depends on the nature of such group. Typical examples are the removal of a trityl group under acidic conditions, for example with aqueous formic acid in tetrahydrofuran (THF) under reflux or the removal of a tert-butoxycarbonyl group with trifluoroacetic acid in dichloromethane at room temperature or the removal of a substituted silyl group with tetrabutylammonium fluoride in aqueous THF at room temperature. An allyl group can smoothly be removed by treating the substrate with catalytic amounts of a palladium complex, e.g. Pd(PPh$_3$)$_4$ in dichloromethane in the presence of an allyl-acceptor such as 1,3-dimethylbarbituric acid.

Scheme 2

The compounds of the present invention wherein "V" is —NH—, and W is a single bond or —CH$_2$— can be prepared according to scheme 2, and are named Ib.

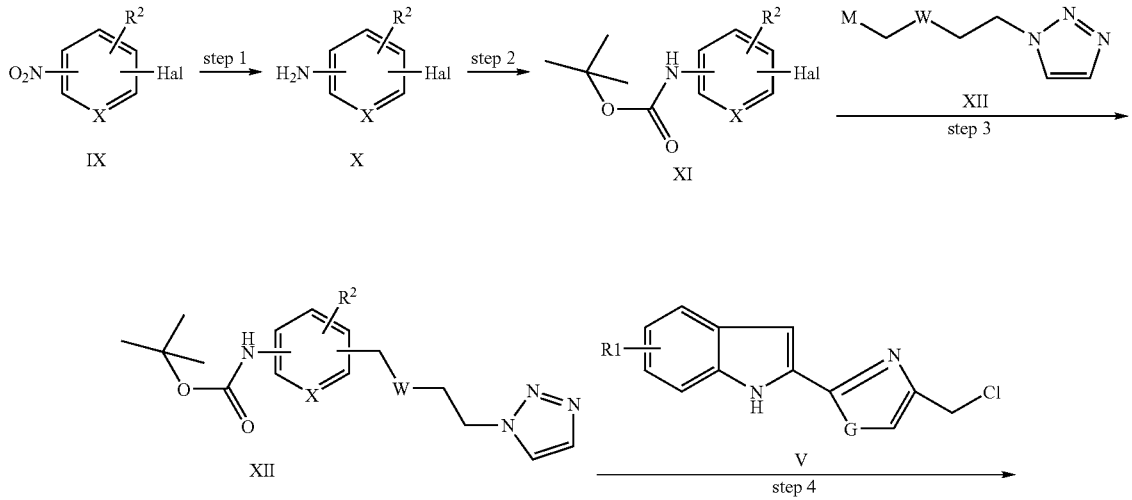

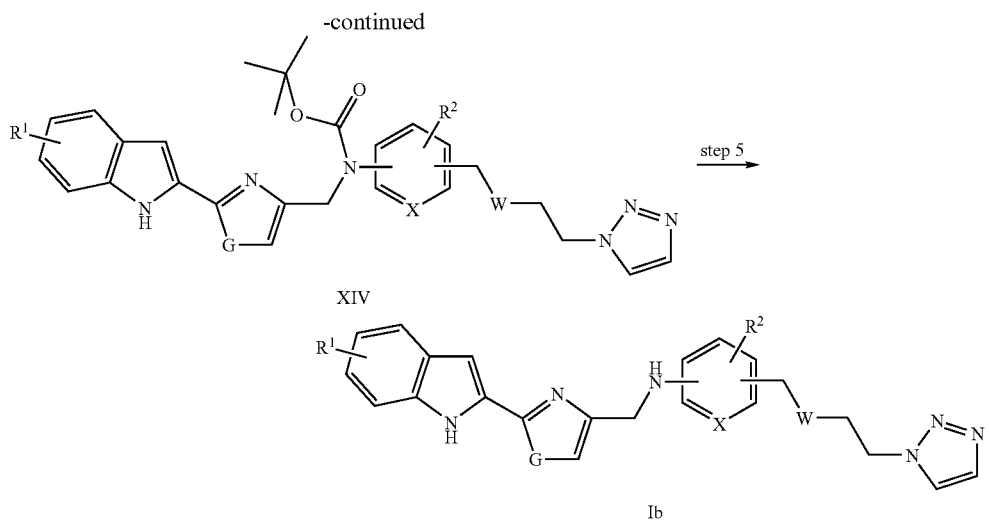

In scheme 2, G, X, R¹ and R² have the significance as given above for formula I, W is a single bond or —CH₂—, M represents BR₂, ZnHal or SnR₃ wherein Hal is halogen like bromine or iodine and R is alkyl or aryl, or the residues R in BR₂ form together with the boron atom, to which they are attached a polycyclic ring system (e.g. BR₂ can represent 9-Bora-bicyclo[3.3.1]non-9-yl or benzo[1,3,2]dioxaborol-2-yl). A method for the synthesis of compounds of formula Ib starts from nitro-derivatives of formula IX. Step 1 of the reaction sequence represents the conversion into amino-derivatives of formula X, using methods well known to someone skilled in the art. For this purpose compounds of formula IX are e.g. hydrogenated in the presence of a palladium catalyst in solvents like methanol or acetic acid at temperatures varying from 30° C. to 100° C. Other commonly used methods employ Sn/HCl, Zn/AcOH or lithium aluminum hydride.

In step 2 of the reaction sequence a suitable protecting group is introduced into compounds of formula X to produce N-protected derivatives of formula XI, using methods well known to someone skilled in the art. Typically compounds of formula X are treated with di-tert-butyl dicarbonate in the presence of base. Typical bases for this reaction are lithium hexamethyldisilazide, lithium diisopropylamide or sodium hydride. Typically solvents like THF or DMF are used at temperatures varying from −78° C. to 40° C. in this reaction.

In step 3, scheme 2 of the reaction sequence compounds of formula XI are reacted with organometallic intermediates of formula XII in a cross coupling reaction, using methods well known to someone skilled in the art. Typically a Suzuki cross coupling strategy was employed for the synthesis of compounds of formula XIII. For this purpose, compounds of formula XII were generated by hydroboration of the corresponding terminal olefins with 9-BBN (9-Borabicyclo [3.3.1]nonane), catechol borane (benzo[1,3,2]dioxaborol) or the like in solvents like THF or DMF at temperatures varying from −30° C. to 100° C. This solution is typically added to a solution of compounds of formula XI in the presence of a palladium catalyst and a base. Typically used catalysts are Pd(PPh₃)₄, (Ph₃P)₂PdCl₂ or Pd(dppf)Cl₂. Typically used bases are sodium carbonate, cesium carbonate or sodium hydroxide in mixtures of e.g. THF or DMF and water. Temperatures vary from −30 to 100° C.

In case X is =C— an alternative route can be followed starting from the commercially available 4-(4-nitrophenyl)-1-butanol, wherein the hydroxyl group is activated as a leaving group e.g. with methylsulfonyl chloride to yield the corresponding methylsulfonate. Then this intermediate is reacted with 1H-[1,2,3]triazole in an alkylation reaction (analogously to step 5 in scheme 1). The resulting 1-[4-(4-Nitro-phenyl)-butyl]-1H-[1,2,3]triazole is reduced to the corresponding aniline (see step 1 this scheme) and the amine is protected e.g. by a BOC protecting group (see step 2 this scheme) to give the [4-(4-[1,2,3]Triazol-1-yl-butyl)-phenyl]-carbamic acid tert-butyl ester. Then the reaction sequence is carried on with step 4.

In case X is =N— the compounds of formula XI can be alternatively reacted with 1-But-3-ynyl-1H-[1,2,3]triazole in a Sonogashira cross-coupling reaction in the presence of catalytic amounts of copper iodide and a palladium complex, e.g. Pd(PPh₃)₄, Pd(PPh₃)₂Cl₂ or the like. The reaction is carried out in the presence of a base like triethyl amine, diisopropyl amine, isopropyl amine, piperidine, morpholine or pyrrolidine and in solvents like THF, DMF or mixtures thereof at temperatures varying from 20° C. to 100° C. yielding the corresponding alkynes which are subsequently reduced to the compounds of formula XIII. Preferably, as reduction reaction a catalytic hydrogenation is performed using catalytic species like palladium on activated charcoal, nickel or platinum. The reaction is typically carried out at temperatures between 0° C. and 50° C., at hydrogen pressures between 1 to 4 atm in solvents like methanol, ethanol, tetrahydrofuran, acetone, ethyl acetate or mixtures thereof.

In step 4, scheme 2 the protected aniline derivatives of formula XIV can be obtained by reactions well known to someone skilled in the art, e.g. by alkylation of the protected anilines of formula XIII with compounds of formula V (see scheme 1). Typically the alkylation is carried out in solvents like DMF, THF, methanol, ethanol and isopropanol. Typical bases for this reaction are sodium hydride, sodium methylate, or lithium diisopropyl amide. The reaction temperatures may vary from −30° C. to 150° C.

In step 5, scheme 2 compounds of formula Ib are generated by deprotection of compounds of formula XIV. Deprotection is achieved by reactions well known to someone skilled in the art, e.g. acid treatment of compounds of formula XIV. Typically used acids include trifluoroacetic acid, acetic acid or hydrochloric acid in solvents like dichloromethane, chloroform or the like at temperatures between −30° C. and 100° C.

Scheme 3

The compounds of the present invention, wherein "V" is —SO$_2$— and W is a single bond or —CH$_2$—, can be prepared according to scheme 3, and are named Ic.

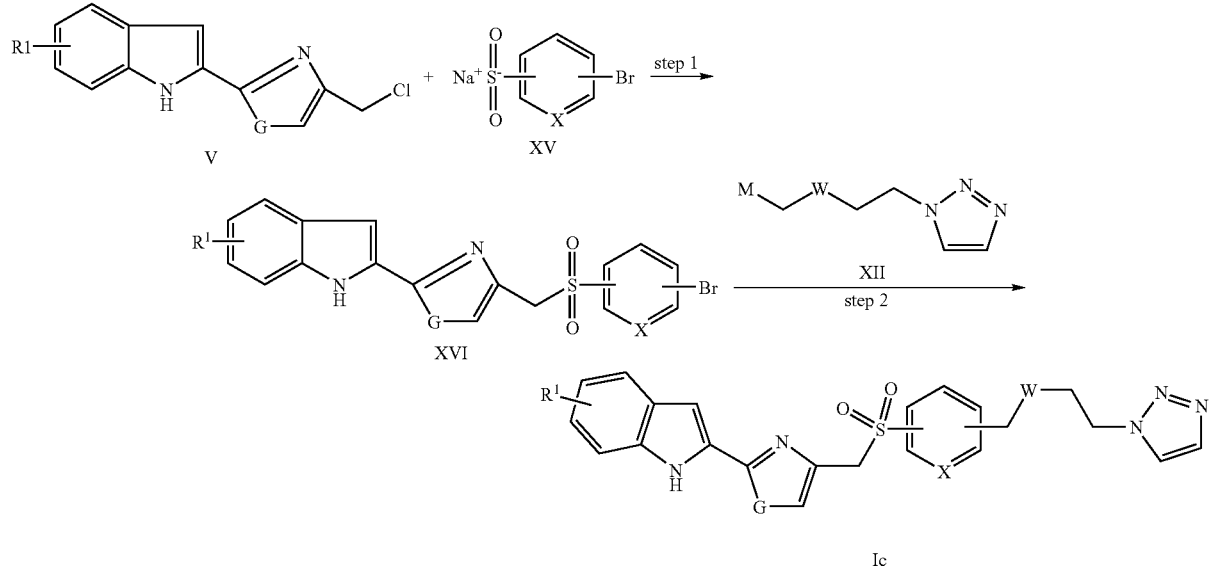

Scheme 3

In scheme 3, G, X, R$^1$ and R$^2$ have the significance as given above for formula I, W is a single bond or —CH$_2$—, M represents BR$_2$, ZnHal or SnR$_3$ wherein Hal is halogen like bromine or iodine and R is alkyl or aryl, or the residues R in BR$_2$ form together with the boron atom, to which they are attached a polycyclic ring system (e.g. BR$_2$ can represent 9-Bora-bicyclo[3.3.1]non-9-yl or benzo[1,3,2]dioxaborol-2-yl). A method for the synthesis of compounds of formula Ic starts from sulfinic acid salts of formula XV. Step 1 of the reaction sequence involves the alkylation of sulfinates of formula XV using methods well known to someone skilled in the art. Typically compounds of formula V (see scheme 1) and compounds of formula XV are heated in solvents like DMF, dimethylsulfoxide (DMSO) or the like at temperatures varying from 30° C. to 130° C. to yield compounds of formula XVI.

The intermediates of formula XVI are also an objective of the invention.

In step 2, scheme 3 of the reaction sequence compounds of formula XVI are reacted with organometallic intermediates of formula XII in a cross coupling reaction, using methods well known to someone skilled in the art. Typically a Suzuki cross coupling strategy is employed for the synthesis of compounds of formula Ic. For this purpose, compounds of formula XII are generated by hydroboration of the corresponding terminal olefins with 9-BBN (9-Borabicyclo[3.3.1]nonane), catechol borane (benzo[1,3,2]dioxaborol) or the like in solvents like THF or DMF at temperatures varying from −30° C. to 100° C. This solution is typically added to a solution of compounds of formula XVI in the presence of a palladium catalyst and a base. Typically used catalysts are Pd(PPh$_3$)$_4$, (Ph$_3$P)$_2$PdCl$_2$ or Pd(dppf)Cl$_2$. Typically used bases are sodium carbonate, cesium carbonate or sodium hydroxide in mixtures of e.g. THF or DMF and water. Temperatures vary from −30 to 100° C.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

The compounds of formula I and their pharmaceutically acceptable salts possess valuable pharmacological properties. It has been found that said compounds inhibit the HER-signaling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signaling pathway inhibitors is demonstrated by the following biological assay:

Viability Assay of HEK293 Cells

A viability assay was performed using the CellTiter-Glo® Luminescent Cell Viability Assay (see Promega Corporation's Technical Bulletin No. 288, pp. 1-11 [revised 2/04] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HEK293 cells (human embryonic kidney cell line transformed by Adenovirus 5 fragments, ATCC-No. CRL 1573) were cultivated in Dulbecco's Modified Eagle Medium (D-MEM) (1×) liquid (high glucose) (which includes L-Alanyl-L-Glutamine [a stabilized a form of L-Glutamine], 4500 mg/L glucose, and 110 mg/L sodium pyruvate) from Invitrogen Coropration (Invitrogen Catalog Number 31966-021 [now 10569-010] which is hereby incorporated by reference), 5% Fetal Calf Serum (FCS, Sigma Cat-No. F4135 (FBS)), 100 Units/ml penicillin/100 µg/ml streptomycin (=Pen/Strep from Invitrogen Cat. No. 15140). For the assay the cells were seeded in 384 well plates, 5000 cells per well, in the same medium. The next day the test compounds were added in various concentrations ranging from 3 µM to 0.00015 µM (10 concentrations, 1:3 diluted).

After 7 days the above viability assay was performed in accordance with the following steps:

Step 1: The cell-plate was equilibrated to room temperature for approximately 30 minutes and than the assay reagent was added.

Step 2: The contents were carefully mixed for 15 minutes to induce cell lysis.

Step 3: After 45 minutes the luminescent signal was measured in Victor 2, (a scanning multiwell spectrophotometer, Wallac).

Details:

1. Day:

Medium: Dulbecco's Modified Eagle Medium (D-MEM) (1×) liquid (high glucose) (which includes L-Alanyl-L-Glutamine [a stabilized a form/source of L-Glutamine], 4500 mg/L glucose, and 110 mg/L sodium pyruvate) from Invitrogen Coropration (Invitrogen Catalog Number 31966-021 [now 10569-010] which is hereby incorporated by reference in its entirety), 5% Fetal Calf Serum (FCS, Sigma Cat-No. F4135 [FBS] which is hereby incorporated by reference in its entirety), Pen/Strep contaning 100 Units/ml penicillin/100 µg/ml streptomycin (Invitrogen Catalog Number 15140, which is hereby incorporated by reference in its entirety). —HEK293 (ATCC-No. CRL 1573): 5000 cells in 60 µl per well of 384 well plate (Greiner 781098, white plates)

Incubate 24 h at 37° C., 5% $CO_2$

2. Day: Induction (Substance Testing):

In general the dilution steeps are 1:3 a) Add 8 µl of 10 mM stock solution of compound to 72 µl DMSO b) dilute 9×1:3 (always 30 µl to 60 µl DMSO) in this DMSO dilution row (results in 10 wells with concentrations from 1000 µM to 0.06 µM)

c) dilute each concentration 1: 4.8 (10 µl compound dilution to 38 µl medium)

d) dilute each concentration 1:10 (10 µl compound dilution to 90 µl medium)

e) add 10 µl of every concentration to 60 µl medium in the cell plate resulting in final concentration of DMSO: 0.3% in every well and resulting in final concentration of compounds from 3 µM to 0.00015 µM Incubate 168 h (7 days) at 37° C., 5% $CO_2$ Analysis:

Add 30 µl of reagent cited above (containing luciferase, luciferan substrate, and buffer), shake 15 minutes at room temperature incubate further 45 minutes at room temperature without shaking.

Measurement:

Victor 2 scanning multiwell spectrophotometer (Wallac), Luminescence mode

Determine IC50 by curve fitting using XLfit® software [(ID Business Solution Ltd., Guilford, Surrey, UK) which his hereby incorporated by reference in its entirety].

With all compounds a significant inhibition of HEK293 cell viability was detected, which is exemplified by the compounds shown in Table 1.

TABLE 1

| Examples | IC50 HEK293 [nM] |
|---|---|
| Results: | |
| 3 | 6.6 |
| 24 | 37 |
| 1, 2, 4, 7, 8, 10, 11, 16, 17, 23, 29, 32, 33, 40 | 0.1-50 |
| 13, 18, 21, 22, 35, 38 | 50-500 |
| 12, 14 | 500-1000 |

In Vivo Assay on Tumor Inhibition:

To generate primary tumors, Non-Small-Cell Lung Cancer (NSCLC) (e.g. Calu-3 (ATTC HTB-55) or A549 (ATTC CCL-185)) cells (4-5.0×10$^6$ in a volume of 100 µl) are injected subcutaneously into the left flank of female SCID beige mice (Severe Combined Immunodeficient/beige mice available from Charles River, Sulzfeld, Germany) or BALB/c nude mice (BALB/c Nude Spontaneous Mutant Mice (homozygotes) available from Taconic Europe, Ry, Denmark). The cells are thawed and expanded in vitro before use in the experiment. Mice are assigned to the treatment groups 14-21 days after cell injection. For grouping (n=10-15 mice per group), the animals are randomized to get a similar mean primary tumor volume of ca. 100-150 mm$^3$ per group. The test compounds are administered orally once per day as a suspension in 7.5% gelatine 0.22% NaCl with an administration volume of 10 ml/kg based on actual body weights. Treatment is initiated one day after staging, and carried out until day 20-50, the final day of the study. The subcutaneous primary tumors are measured twice weekly, starting prior to randomization, in two dimensions (length and width) using an electronic caliper. The volume of the primary tumor is calculated using the formula: V[mm$^3$]=(length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions may comprise, for example, the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes(here 1 ml steps) until final volume is reached or extract is clear.
10. Fill up to final volume with gelatin and homogenize.

The above described preparation yields micro-suspensions of the compounds of formula I with particle sizes between 1 and 10 μm. The suspensions are suitable for oral applications and can be used in the in vivo assay described above.

Pharmaceutical compositions containing a compound of the present invention or a pharmaceutically acceptable salt thereof and a therapeutically inert carrier are also an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

In accordance with the invention the compounds of the present invention as well as their pharmaceutically acceptable salts are useful in the control or prevention of illnesses. Based on their HER-signaling pathway inhibition and their antiproliferative activity, said compounds are useful for the treatment of diseases such as cancer in humans or animals and for the production of corresponding pharmaceutical compositions. The dosage depends on various factors such as the manner of administration, species, age and/or individual state of health.

Another embodiment of the invention is a pharmaceutical composition, containing one or more compounds of formula I together with pharmaceutically acceptable excipients.

Still another embodiment of the invention is said pharmaceutical composition for the inhibition of tumor growth.

Still another embodiment of the invention is the use of a compound of formula I for the treatment of cancer.

Still another embodiment of the invention is the use of a compound of formula I for the manufacture of corresponding pharmaceutical compositions for the inhibition of tumor growth.

The following examples and references are provided to aid the understanding of the present invention, the true scope of which is set forth in the appended claims. It is understood that modifications can be made in the procedures set forth without departing from the spirit of the invention.

EXPERIMENTAL PROCEDURES

A: Starting Materials

Preparation of [4-(4-[1,2,3]triazol-1-yl-butyl)-phenyl]-carbamic acid tert-butyl ester i) 1-[4-(4-Nitro-phenyl)-butyl]-1H-[1,2,3]triazole A solution of p-nitrophenylbutanol (5 g, 25.61 mmol) in ethyl acetate (200 ml) is treated with methanesulfonyl chloride (3.52 g, 30.73 mmol) at 0° C. The resulting suspension is stirred for 30 min at this temperature and for 1 h at room temperature. The mixture is washed with ice water and brine, dried over Na$_2$SO$_4$ and evaporated to dryness. The resulting oily residue crystallizes on cooling yielding 7.62 g of a yellow solid.

To a suspension of the mesylate (6.53 g, 23.9 mmol) in 2-methyl-2-butanol (100 ml) 1H-[1,2,3]triazole (2.46 g, 35.6 mmol), KI (0.392 g, 23.6 mmol) and NaOH (1.44 g, 36 mmol) are added and the mixture stirred for 3 h at room temperature. After evaporation of the solvent the mixture is taken up in toluene (150 ml) and washed with water. The toluene layer is evaporated to dryness and the residue dissolved in ethyl acetate/isopropyl ether (2/1, 15 ml) followed by the addition of methane sulfonic acid (0.3 g). After stirring for 1 h at room temperature the resulting precipitate is filtered, washed with ethyl acetate/isobutyl ether (1:1) and dried yielding 1-[4-(4-nitro-phenyl)-butyl]-1H-[1,2,3]triazole methanesulfonate as a yellow solid which can be used without further purification. Yield 3.5 g (55.5%)

MS: M=246.2 (API+)

$^1$H-NMR (400 MHz, CDCl$_3$): 1.67 (m, 2H), 1.96 (m, 2H), 2.76 (t, 2H), 4.43 (t, 2H), 7.30 (d, 2H), 7.55 (s, 1H), 7.70 (s, 1H), 8.12 (d, 2H)

ii) 4-(4-[1,2,3]Triazol-1-yl-butyl)-phenylamine

1-[4-(4-Nitro-phenyl)-butyl]-1H-[1,2,3]triazole (2.89 g, 11.74 mmol) is hydrogenated in a mixture of methanol/THF (1:1, 50 ml) in the presence of palladium on charcoal (10%, 0.5 g) for 5 h. After filtration solvents are removed in vacuo yielding 4-(4-[1,2,3]triazol-1-yl-butyl)-phenylamine as a yellow gum. Yield 2.03 g (80%)

MS: M=217.3 (API+)

$^1$H-NMR (400 MHz, CDCl$_3$): 1.62 (m, 2H), 1.91 (m, 2H), 2.63 (t, J=7.5 Hz, 2H), 4.38 (t, J=7.0 Hz, 2H), 7.15 (d, J=8.3 Hz, 2H), 7.41 (d, J=8.3 Hz, 2H), 7.52 (s, 1H), 7.69 (s, 1H)

iii) [4-(4-[1,2,3]Triazol-1-yl-butyl)-phenyl]-carbamic acid tert-butyl ester

To a solution of 10.0 g (46.2 mmol) 4-(4-[1,2,3]triazol-1-yl-butyl)-phenylamine in 100 ml THF were added at 0° C. 92.5 ml of a 1 M solution of bis-trimethylsilyl lithiumamide in THF and thereafter at room temperature a solution of 9.08 g (41.6 mmol) di-tert-butyl dicarbonate in THF. After stirring for 30 min, the mixture was quenched with ammonium chloride solution and extracted with ethyl acetate. The extract was dried, evaporated and the residue purified on silica. Elution with ethyl acetate yielded 12.0 g (82%) title compound as slightly yellow crystals.

MS: M=317.3 (API+)

$^1$H-NMR (400 MHz, CDCl$_3$): 1.62 (m, 2H), 1.51 (s, 1H), 1.91 (m, 2H), 2.59 (t, 2H), 4.37 (t, 2H), 6.57 (s, 1H), 7.05 (d, 2H), 7.27 (d, 2H), 7.49 (s, 1H), 7.68 (s, 1H)

Preparation of 4-(2-[1,2,3]Triazol-1-yl-ethoxymethyl)-phenol i) 1-Allyloxy-4-chloromethyl-benzene 7.67 g (67.0 mmol) methanesulfonyl chloride were given at 0° C. to a solution of 10.0 g (60.9 mmol) (4-allyloxy-phenyl)-methanol and 9.34 ml (67.0 mmol) triethylamine in 35 ml dichloromethane and stirred at r.t. overnight. The mixture was poured in ice water, extracted with dichloromethane and the organic phase dried over Na$_2$SO$_4$. After removal of solvents the residue was purified by chromatography on silica gel (ethyl acetate/n-heptane 1:5) to yield 3.12 g (28%) pale yellow oil.

$^1$H-NMR(400 MHz, [D$_6$]-DMSO): δ=4.57(m, 2H, OCH$_2$), 4.72(s, 2H, CH$_2$Cl), 5.26(d, 1H, =CH$_2$), 5.39(d, 1H, =CH$_2$), 6.04(m, 1H, CH=CH$_2$), 6.95(d, 2H, 2'-/6'-H), 7.35(d, 2H, 3'-/5'-H).

ii) 1-[2-(4-Allyloxy-benzyloxy)-ethyl]-1H-[1,2,3]-triazole 197 mg (8.21 mmol) 95% sodium hydride were given at −50° C. to a solution of 1.00 g (5.47 mmol) 1-allyloxy-4-chloromethyl-benzene and 619 mg (5.47 mmol) 2-(1H-[1,2,3]-triazol-1-yl)-ethanol in 9.0 ml DMF. The mixture was allowed to warm slowly to r.t., stirred overnight and 10 ml water was added. The formed oil was collected with 10 ml dichloromethane, the aqueous phase extracted with 10 ml dichloromethane and the combined organic phases dried over Na$_2$SO$_4$.

Solvents were removed in vacuum and the residue purified by chromatography on silica gel (ethyl acetate/heptane 1:1) to yield 1.10 g (78%) yellow oil.

MS: M=260.3 (API+), 258.3 (API−).

$^1$H-NMR(400 MHz, [D$_6$]-DMSO): δ=3.79(t, 2H, CH$_2$—CH$_2$-triazole), 4.39(s, 2H, OCH$_2$Ph), 4.54-4.59(m, 4H, OCH$_2$-vinyl, CH$_2$-triazole), 5.25(d, 1H, =CH$_2$), 5.38(d, 1H, =CH$_2$), 6.06(m, 1H, CH=CH$_2$), 6.89(d, 2H, 2'-/6'-H), 7.15(d, 2H, 3'-/5'-H), 7.16(s, 1H, triazole), 8.08(s, 1H, triazole).

iii) 4-(2-[1,2,3]Triazol-1-yl-ethoxymethyl)-phenol

A solution of 500 mg (1.93 mmol) 1-[2-(4-allyloxy-benzyloxy)-ethyl]-1H-[1,2,3]-triazole in 10 ml dichloromethane was added to a solution of 904 mg (5.79 mmol) 1,3-dimethylbarbituric acid and 58 mg (0.05 mmol) Pd(PPh$_3$)$_4$ in 20 ml dichloromethane and stirred for 4.5 h at 40° C. The mixture was extracted with 3×20 ml sat. NaHCO$_3$-solution and 8 ml water and the combined aqueous phases were reextracted with 2×10 ml dichloromethane. The organic extracts were combined and dried over MgSO$_4$. Solvents were distilled off and the residue purified by chromatography on silica gel (ethyl acetate) to yield 248 mg (59%) of the title compound.

$^1$H-NMR(400 MHz, [D$_6$]-DMSO): δ=3.77(t, 2H, CH$_2$—CH$_2$-triazole), 4.33(s, 2H, OCH$_2$Ph), 4.56(t, 2H, CH$_2$-triazole), 6.69(d, 2H, 2'-/6'-H), 7.03(d, 2H, 3'-/5'-H), 7.11(s, 1H, triazole), 8.07(s, 1H, triazole), 9.37(s, 1H, PhOH).

Preparation of 4-(2-[1,2,3]Triazol-1-yl-ethanesulfinylmethyl)-phenol i) (4-Allyloxy-phenyl)-methanethiol A mixture of 2.00 g (10.9 mmol) 1-allyloxy-4-chloromethyl-benzene and 917 mg (12.1 mmol) thiourea in 3.0 ml ethanol was heated to reflux for 7 h. Solvents were distilled off and the crystalline residue was washed with cold ethanol and isolated by filtration. After addition of 2.5 ml ethanol, 1.0 ml water and 0.7 ml 25% aqueous ammonia, the mixture was heated to reflux for 1 h. Ethanol was distilled off, then acidified with 0.5 ml half conc. HCl and extracted with ethyl acetate. The solution was dried over MgSO4 and solvents were removed in vacuo to yield 1.59 g (81%) colourless oil, which was used immediately.

¹H-NMR(400 MHz, [D₆]-DMSO): δ=2.75 (s, 1H, SH), 3.68(s, 2H, CH₂SH), 4.54(m, 2H, OCH₂-vinyl), 5.26(d, 1H, =CH₂), 5.38(d, 1H, =CH₂), 6.05(m, 1H, CH=CH₂), 6.89 (d, 2H, 2'-/6'-H), 7.24(d, 2H, 3'-/5'-H).

ii) Toluene-4-sulfonic acid 2-[1,2,3]triazol-1-yl-ethyl ester

A solution of 12.9 g (66.3 mmol) p-toluenesulfonic acid chloride, 2.03 g (16.6 mmol) 4-(N,N-dimethylamino)-pyridine and 11.2 ml (80.2 mmol) triethylamine in 150 ml dichloromethane was cooled to −10° C. A solution of 7.50 g (66.3 mmol) 2-(1H-[1,2,3]triazol-1-yl)-ethanol in 150 ml dichloromethane was added dropwise and the mixture stirred overnight at −4° C. 170 ml Ice and 170 ml dichloromethane were added and stirring continued for 10 min. followed by addition of 3.9 ml conc. HCl. The organic phase was separated, washed with sat. NaHCO₃-solution and brine, dried over Na₂SO₄ and solvents distilled off. Yield 15.3 g (86%) orange crystals.

¹H-NMR(400 MHz, [D₆]-DMSO): δ=2.41(s, 3H, CH₃), 4.41(t, 2H, CH₂—OTos), 4.67(t, 2H, CH₂-triazole), 7.44(d, 2H, Ar—H), 7.65(d, 2H, Ar—H), 7.69(s, 1H, triazole), 8.03(s, 1H, triazole).

iii) 1-[2-(4-Allyloxy-benzylsulfanyl)-ethyl]-1H-[1,2,3]triazole 1.58 g (6.14 mmol) (4-allyloxy-phenyl)-methanethiol and 1.64 g (6.14 mmol) toluene-4-sulfonic acid 2-[1,2,3]triazol-1-yl-ethyl ester were dissolved in 15 ml DMF and cooled to −30° C. 294 mg (12.3 mmol) 95% Sodium hydride were added, the mixture allowed to warm to r.t. and stirred for 12 h. 10 ml Water were added and the residue dissolved in dichloromethane. The organic phase was dried over Na₂SO₄, solvents removed and the remaining material purified by chromatography on silica gel (ethyl acetate/n-heptane 1:1) to yield 1.33 g (79%) yellow oil.

MS: M=298.0 (M+Na⁺, API+).

¹H-NMR(400 MHz, [D₆]-DMSO): δ=2.86(t, 2H, CH₂—CH₂-triazole), 3.65(s, 2H, OCH₂Ph), 4.55(m, 4H, OCH₂-vinyl, CH₂-triazole), 5.25(d, 1H, =CH₂), 5.38(d, 1H, =CH₂), 6.05(m, 1H, CH=CH₂), 6.90(d, 2H, 2'-/6'-H), 7.22(d, 2H, 3'-/5'-H), 7.73(s, 1H, triazole), 8.12(s, 1H, triazole).

iv) 1-[2-(4-Allyloxy-phenylmethanesulfinyl)-ethyl]-1H-[1,2,3]triazole

A solution of 1.86 g (8.29 mmol) 77% 3-chloroperbenzoic acid in 40 ml ethyl acetate was added at −30° C. within 20 min. to a solution of 1.90 g (6.90 mmol) 1-[2-(4-allyloxy-benzylsulfanyl)-ethyl]-1H-[1,2,3]triazole in 160 ml dichloromethane and stirred for 1 h. The mixture was allowed to warm to room temperature (r.t.) washed with sat. NaHCO₃-solution, water and evaporated. The residue was purified by chromatography on silica gel (ethyl acetate/methanol 5:1) to give 1.25 g of the title compound as white powder.

¹H-NMR(400 MHz, [D₆]-DMSO): δ=3.11(dt, 1H, CH₁—CH₂-triazole), 3.32(dt, 1H, CH₂—CH₂-triazole), 3.94.1(d, 1H, SO₂CH₂Ph), 4.12(d, 1H, SO₂CH₂Ph), 4.56(d, 2H, OCH₂-vinyl), 4.78(m, 2H, CH₂-triazole), 5.26(d, 1H, =CH₂), 5.39(d, 1H, =CH₂), 6.02(m, 1H, CH=CH₂), 6.95 (d, 2H, 2'-/6'-H), 7.22(d, 2H, 3'-/5'-H), 7.75(s, 1H, triazole), 8.16(s, 1H, triazole).

v) 4-(2-[1,2,3]Triazol-1-yl-ethanesulfinylmethyl)-phenol

A solution of 1.00 g (3.43 mmol) 1-[2-(4-allyloxy-phenylmethanesulfinyl)-ethyl]-1H-[1,2,3]triazole in 60 ml dichloromethane was added to a solution of 1.61 g (10.3 mmol) 1,3-dimethylbarbituric acid and 102 mg (0.09 mmol) Pd(PPh₃)₄ in 30 ml dichloromethane and stirred for 5 h at 50° C. The mixture was extracted with 3×50 ml sat. NaHCO₃-solution and 20 ml water. The organic phase was discarded and the aqueous phase acidified with 2M HCl to pH=4, concentrated to a volume of 50 ml and adjusted to pH=1. After five extractions with ethyl acetate, the organic extracts were combined and dried over MgSO₄. After evaporation the residue was purified by chromatography on silica gel (dichloromethane/methanol 100:2) to yield 0.84 g (97%) of the title compound.

¹H-NMR(400 MHz, [D₆]-DMSO): δ=3.11(dt, 1H, CH₂—CH₂-triazole), 3.29(dt, 1H, CH₂—CH₂-triazole), 3.90(d, 1H, SO₂CH₂Ph), 4.06(d, 1H, SO₂CH₂Ph), 4.77(m, 2H, CH₂-triazole), 6.74(d, 2H, 2'-/6'-H), 7.10(d, 2H, 3'-/5'-H), 7.74(s, 1H, triazole), 8.16(s, 1H, triazole), 9.49(s, 1H, OH).

Preparation of 1-but-3-enyl-1H-[1,2,3]triazole

1H-[1,2,3]Triazole (10.36 g, 0.15 mol), sodium hydroxide (6 g, 0.15 mol) and potassium iodide (2.49 g, 0.015 mol) were dissolved in 2-methyl-2-butanol (50 ml) and heated to reflux for 1 h. At this temperature 4-bromo-but-1-ene (20.25 g, 0.15 mol) in 2-methyl-2-butanol (20 ml) was added dropwise and the resulting mixture was heated at reflux temperature for 4 h. After removal of the solvent the residue was taken up in ethyl acetate (100 ml), washed with water (3×50 ml), dried over sodium sulfate and concentrated. The crude product was purified by distillation yielding 0.65 g 2-but-3-enyl-2H-[1,2,3]triazole (b.p. 90-100° C. at 10 mbar), ¹H-NMR (400 MHz, [D₆]-DMSO): δ=2.62(q, 2H, CH₂—CH=CH₂), 4.48(t, 2H, CH₂-triazole), 4.97-5.06(m, 2H, CH₂—CH=CH₂), 5.75(m, 1H, CH₂—CH=CH₂), 7.75 (s, 2H, triazole) and 6.36 g (34%) 1-but-3-enyl-1H-[1,2,3]triazole (b.p. 106-108° C. at 10 mbar) as a colorless liquid.

¹H-NMR (400 MHz, [D₆]-DMSO): δ=2.59(q, 2H, CH₂—CH=CH₂), 4.45(t, 2H, CH₂-triazole), 5.00-5.06(m, 2H, CH₂—CH=CH₂), 5.76(m, 1H, CH₂—CH=CH₂), 7.70 (s, 1H, triazole), 8.10(s, 1H, triazole).

Preparation of 1-but-3-ynyl-1H-[1,2,3]triazole

But-3-yn-1-ol (49.57 g, 707.2 mmol) and triethylamine (107.7 mL, 777 mmol, dried over KOH) were dissolved in dry dichloromethane (500 mL) under a nitrogen atmosphere and cooled to 0° C. Methanesulfonyl chloride (54.8 mL, 708 mmol), dissolved in 500 mL of dry dichloromethane was added within 90 minutes while keeping the temperature below 5° C. The mixture was stirred for 3.5 hours at room temperature, then poured onto 2.5 L of ice water. The organic phase was separated and washed with 2×500 mL of water and 1×250 mL of brine and dried over sodium sulfate. The volatiles were removed to yield 94.18 g of the methane sulfonate (631.2 mmol, 89.2%) as a yellow liquid.

A suspension of NaOH (37.86 g, 946.5 mmol), sodium iodide (94.65 g, 631.5 mmol) and 1H-[1,2,3]Triazole (61.03 g, 883.6 mmol) in 2-methyl-2-butanol (750 mL) was refluxed for 1 h under an inert atmosphere. After cooling to room temperature the methane sulfonate (94.18 g, 631.2 mmol) was added within 5 minutes. The resulting suspension was then heated to reflux for 3 hours, cooled to room temperature and concentrated on a rotary evaporator at 45° C.

Water (500 mL) and dichloromethane (1 L) were added and the organic phase was separated, dried over sodium sulfate and the volatiles removed at 30° C. The residue was distilled at 1.5 mbar. A forerun was collected at 20-70° C. The main fraction distilled at 123-129° C. as a colourless, turbid liquid. After filtration over Celite 1-But-3-ynyl-1H-[1,2,3]triazole was obtained as a colourless liquid (29.8 g, 40%). The content according to GC/FID was >98%.

$^1$H-NMR (CDCl) δ=2.05 (t, 1H, C—CH), 2.75 (dt, 2H, C$\underline{H}_2$—C≡CH), 4.5 (t, 2H, CH$_2$-triazole), 7.65 (s, 1H, triazole), 7.70 (s, 1H, triazole).

Preparation of [5-(4-[1,2,3]triazol-1-yl-butyl)-pyridin-2-yl]-carbamic acid tert-butyl ester i) (5-Iodo-pyridin-2-yl)-carbamic acid tert-butyl ester A solution of 26.72 mL of a 1 M solution of bis-trimethylsilyl lithiumamide in THF was added to a solution of 5-iodo-pyridin-2-ylamine (3 g, 13.36 mmol) in anhydrous THF (30 ml) at 0° C. After warming to r.t. a solution of di-tert-butyl dicarbonate (2.77 g, 12.69 mmol) in THF was added and stirring continued for 16 h. The mixture was quenched with ammonium chloride solution and extracted with ethyl acetate. The extract was washed with brine, dried over Na$_2$SO$_4$ and concentrated. The crude product was washed with diethyl ether yielding (5-iodo-pyridin-2-yl)-carbamic acid tert-butyl ester as light orange solid. Yield 3.45 g, (81%)

MS: M=264.7 (ESI+, M−$^t$Bu)
$^1$H-NMR(400 MHz, CDCl$_3$): δ=1.55 (s, 9H), 7.84 (d, 1H), 7.90 (d, 1H), 8.47 (s, 1H), 8.49 (s, 1H)

ii) [5-(4-[1,2,3]Triazol-1-yl-but-1-ynyl)-pyridin-2-yl]-carbamic acid tert-butyl (5-Iodo-pyridin-2-yl)-carbamic acid tert-butyl ester (3.45 g, 10.77 mmol) was dissolved in anhydrous THF (30 ml) under an argon atmosphere and treated with (PPh$_3$)$_2$Pd(II)Cl$_2$ (0.6 g, 0.86 mmol) and copper iodide (0.2 g, 1.1 mmol). To this mixture a solution of 1-but-3-inyl-1H-[1,2,3]triazole (2.1 g, 17.24 mmol) in anhydrous THF (20 ml) is added dropwise at 0° C. followed by diisopropyl-amine (7.6 mL, 53.88 mmol). After stirring for 6 h at room temperature ethyl acetate (100 mL) was added, the mixture was washed with water, brine and dried over sodium sulfate. After removal of the solvents the crude product was purified by column chromatography on silica gel (dichloro methane/methanol 98:2) yielding [5-(4-[1,2,3]triazol-1-yl-but-1-ynyl)-pyridin-2-yl]-carbamic acid tert-butyl ester as light yellow solid (2.35 g, 70%).

MS: M=314.0 (ESI+)
$^1$H-NMR(400 MHz, CDCl$_3$): δ=1.53 (s, 9H), 3.04 (t, 2H), 4.62 (t, 2H), 7.61 (d, 1H), 7.71 (m, 2H), 7.91 (d, 1H), 8.05 (s, 1H), 8.27 (s, 1H)

iii) [5-(4-[1,2,3]Triazol-1-yl-butyl)-pyridin-2-yl]-carbamic acid tert-butyl ester To a solution of [5-(4-[1,2,3]triazol-1-yl-but-1-ynyl)-pyridin-2-yl]-carbamic acid tert-butyl (0.87 g, 2.77 mmol) in THF/methanol (1:1, 30 mL) palladium on charcoal (10%, 0.25 g) was added and the mixture hydrogenated at room temperature for 4 h. After filtration and evaporation of the solvents [5-(4-[1,2,3]Triazol-1-yl-butyl)-pyridin-2-yl]-carbamic acid tert-butyl ester was isolated as light yellow solid (0.84 g, 95%).

MS: M=279 (ESI+, M−$^t$Bu)
$^1$H-NMR(400 MHz, CDCl$_3$): δ=1.52 (s, 9H), 1.62 (m, 2H), 1.95 (m, 2H), 2.59 (t, 2H), 4.40 (t, 2H), 7.44 (d, 1H), 7.49 (s, 1H), 7.67 (s, 1H), 7.67 (s, 1H), 7.85 (d, 1H), 8.03 (s, 1H)

Preparation of [2-Fluoro-4-(4-[1,2,3]triazol-1-yl-butyl)-phenyl]-carbamic acid tert-butyl ester To a solution of 1-but-3-enyl-1H-[1,2,3]triazole (0.85 g, 6.9 mmol) in THF (15 ml) 9-borabicyclo[3.3.1]nonane (0.5 M in THF, 30.3 ml, 15.2 mmol) was added dropwise at 0° C. and stirring continued for 2 h. This mixture was then added to a solution of (4-bromo-2-fluoro-phenyl)-carbamic acid tert-butyl ester (2 g, 6.89 mmol), Pd(dppf)Cl$_2$ (0.56 g, 0.69 mmol) and aqueous cesium carbonate (6.89 ml, 3M) in DMF (30 ml) and stirred for 3 h at 70° C. Water (100 ml) was added and the mixture extracted with ethyl acetate (3×100 ml). The combined organic layers were washed with water and brine, dried over sodium sulfate and concentrated. The crude product was purified on silica gel (ethyl acetate) to yield [2-Fluoro-4-(4-[1,2,3]triazol-1-yl-butyl)-phenyl]-carbamic acid tert-butyl ester as light yellow solid. Yield 1.93 g (84%)

MS: M=335 (API+)
$^1$H-NMR(400 MHz, CDCl$_3$): δ=1.52 (s, 9H), 1.61 (m, 2H), 1.92 (m, 2H), 2.59 (t, 2H), 4.38 (t, 2H), 6.61 (br, 1H), 6.81-6.88 (m, 2H), 7.49 (s, 1H), 7.70 (s, 1H), 7.94 (br, 1H)

Preparation of 2-(4-Chloromethyl-oxazol-2-yl)-5-trifluoromethoxy-1H-indole (i) 5-Trifluoromethoxy-1H-indole-2-carboxylic acid amide Oxalyl chloride (2.63 ml, 30.6 mmol) was added dropwise at 0° C. within 45 min. to a suspension of 5-trifluoromethoxy-1H-indole-2-carboxylic acid (5 g, 20.4 mmol) in THF (20 ml) and N,N-dimethyl formamide (0.5 ml). Stirring was continued at 0-5° C. for 30 min. and thereafter for 3 h at room temperature. The resulting solution was cooled to 0-5° C. again and then added within 15 min. to 75 ml of a 25% aqueous solution of ammonia. After stirring for 30 min. the precipitated amide was collected, washed with water and dried at 40° C. in vacuo yielding 5-trifluoromethoxy-1H-indole-2-carboxylic acid amide as off white solid. Yield 5 g (100%)

MS: M=245.0 (ESI+)

(ii) 2-(4-Chloromethyl-oxazol-2-yl)-5-trifluoromethoxy-1H-indole 5-trifluoromethoxy-1H-indole-2-carboxylic acid amide (4.5 g, 18.43 mmol) and dichloro acetone (3.5 g, 27.63 mmol) in toluene/DMF (5:1, 30 ml) were kept at reflux temperature for 24 h with continuous removal of water by applying a Dean-Stark trap (a water separator used in chemical reactions). After removal of solvents in vacuo, the residue was intensively shaken with water, the precipitate was isolated by filtration and washed with water and brine. After evaporation of the solvents in vacuo chromatography on silica gel (iso-hexanes/ethyl acetate 3:1) yielded 2-(4- chloromethyl-oxazol-2-yl)-5-trifluoromethoxy-1H-indole as off white solid. Yield 2.6 g (44%)

MS: M=317.0 (API+).

$^1$H-NMR(400 MHz, [D$_6$]-DMSO): δ=4.57 (s, 2H), 7.13 (s, 1H), 7.15 (d, 1H), 7.38 (d, 1H), 7.53 (s, 1H), 7.72 (s, 1H), 9.11 (br, 1H)

Preparation of 2-[4-(4-bromo-benzenesulfonylmethyl)-oxazol-2-yl]-5-trifluoromethoxy-1H-indole A solution of 2-(4-chloromethyl-oxazol-2-yl)-5-trifluoromethoxy-1H-indole (0.3 g, 0.95 mmol) and 4-bromobenzenesulfinic acid sodium salt (0.92 g, 3.8 mmol) in N,N-dimethyl formamide (10 ml) was stirred for 16 h at 60° C. After cooling the mixture was poured on water (20 ml) and extracted with ethyl acetate (3×20 ml). The combined organic extracts were dried over sodium sulfate and concentrated in vacuo. Chromatography on silica gel (ethyl acetate/iso-hexanes 1:1) yielded the title compound as tan solid. Yield 0.28 g (59%)

MS: M=500.9/502 (ESI+)

$^1$H-NMR(400 MHz, CDCl$_3$): δ=4.39 (s, 2H), 7.09 (s, 1H), 7.16 (d, 1H), 7.38 (d, 1H), 7.52 (s, 1H), 7.67-7.73 (m, 5H), 8.98 (br, 1H)

B: Final products

EXAMPLE 1

2-{4-[4-(4-[1,2,3]Triazol-1-yl-butyl)-phenoxymethyl]-oxazol-2-yl}-5-trifluoromethoxy-1H-indole Sodium hydride (7 mg, 0.28 mmol) was given at 0° C. to a solution of 4-(4-[1,2,3]triazol-1-yl-butyl)-phenol (55 mg, 0.25 mmol) in 2.0 ml N,N-dimethyl formamide and stirred for 30 min. 2-(4-Chloromethyl-oxazol-2-yl)-5-trifluoromethoxy-1H-indole (80 mg, 0.25 mmol) dissolved in 1.0 ml N,N-dimethyl formamide was added at 0° C. and stirring continued at 0° C. for 1 h and 12 h at room temperature thereafter. The mixture was quenched with water (10 ml) and extracted with ethyl acetate (3×10 ml). The combined organic extracts were washed with brine (10 ml), dried over sodium sulfate and concentrated in vacuo. Chromatography on silica gel (ethyl acetate) yielded 2-{4-[4-(4-[1,2,3]Triazol-1-yl-butyl)-phenoxymethyl]-oxazol-2-yl}-5-trifluoromethoxy-1H-indole as off white solid. Yield 50 mg (40%)

MS: M=498.1 (API+)

$^1$H-NMR(400 MHz, CDCl$_3$): δ=1.62 (m, 2H), 1.94 (m, 2H), 2.60 (t, 2H), 4.39 (t, 2H), 5.04 (s, 2H), 6.92 (d, 2H), 7.07 (d, 2H), 7.13 (s, 1H), 7.14 (d, 1H), 7.39 (d, 1H), 7.51 (d, 2H), 7.70 (s, 1H), 7.74 (s, 1H), 9.24 (br, 1H)

EXAMPLE 2

5-Chloro-2-{4-[4-(4-[1,2,3]triazol-1-yl-butyl)-phenoxymethyl]-oxazol-2-yl}-1H-indole In an analogous manner as described for example 1 5-chloro-2-{4-[4-(4-[1,2,3]triazol-1-yl-butyl)-phenoxymethyl]-oxazol-2-yl}-1H-indole was prepared from the appropriate starting material.

MS: M=448.2 (ESI+)

$^1$H-NMR(400 MHz, DMSO-d$_6$): δ (ppm)=1.48 (m, 2H), 1.82 (t, 2H), 2.51 (m, 2H), 4.39 (t, 2H), 5.04 (s, 2H), 6.96 (d, 2H), 7.09 (m, 3H), 7.21 (d, 1H), 7.44 (d, 1H), 7.70 (s, 2H), 8.10 (s, 1H), 8.32 (s, 1H), 12.30 (br, 1H)

EXAMPLE 3

5-Fluoro-2-{4-[4-(4-[1,2,3]triazol-1-yl-butyl)-phenoxymethyl]-oxazol-2-yl}-1H-indole In an analogous manner as described for example 1 5-Fluoro-2-{4-[4-(4-[1,2,3]triazol-1-yl-butyl)-phenoxymethyl]-oxazol-2-yl}-1H-indole was prepared from the appropriate starting material.

MS: M=432.2 (API+)

$^1$H-NMR(400 MHz, DMSO-d$_6$): δ (ppm)=1.48 (m, 2H), 1.81 (m, 2H), 2.54 (t, 2H), 4.39 (t, 2H), 5.04 (s, 2H), 6.96 (d, 2H), 7.09 (m, 4H), 7.41 (m, 2H), 7.71 (s, 1H), 8.11 (2, 1H), 8.31 (s, 1H), 12.20 (br, 1H)

EXAMPLE 4

6-Fluoro-2-{4-[4-(4-[1,2,3]triazol-1-yl-butyl)-phenoxymethyl]-oxazol-2-yl}-1H-indole In an analogous manner as described for example 1 6-Fluoro-2-{4-[4-(4-[1,2,3]triazol-1-yl-butyl)-phenoxymethyl]-oxazol-2-yl}-1H-indole was prepared from the appropriate starting material.

MS: M=432.1 (API+)

$^1$H-NMR(400 MHz, DMSO-d$_6$): δ (ppm)=1.48 (m, 2H), 1.81 (m, 2H), 2.53 (m, 2H), 4.39 (t, 2H), 5.03 (s, 2H), 6.95 (m, 3H), 7.10 (m, 3H), 7.15 (m, 1H), 7.65 (m, 1H), 7.70 (s, 1H), 8.10 (s, 1H), 8.29 (s, 1H), 12.18 (br, 1H)

EXAMPLE 5

6-Chloro-2-{4-[4-(4-[1,2,3]triazol-1-yl-butyl)-phenoxymethyl]-oxazol-2-yl}-1H-indole In an analogous manner as described for example 1 6-Chloro-2-{4-[4-(4-[1,2,3]triazol-1-yl-butyl)-phenoxymethyl]-oxazol-2-yl}-1H-indole was prepared from the appropriate starting material.

MS: M=448.1 (API+)

$^1$H-NMR(400 MHz, CDCl$_3$): δ (ppm)=1.62 (m, 2H), 1.93 (m, 2H), 2.59 (t, 2H), 4.38 (t, 2H), 5.03 (s, 2H), 6.90 (m, 2H), 7.08 (m, 4H), 7.39 (s, 1H), 7.43 (s, 1H), 7.57 (d, 1H), 7.70 (s, 1H), 7.72 (s, 1H), 9.24 (br, 1H)

EXAMPLE 6

2-{4-[3-Methyl-4-(4-[1,2,3]triazol-1-yl-butyl)-phenoxymethyl]-oxazol-2-yl}-5-trifluoromethoxy-1H-indole In an analogous manner as described for example 1 2-{4-[3-Methyl-4-(4-[1,2,3]triazol-1-yl-butyl)-phenoxymethyl]-oxazol-2-yl}-5-trifluoromethoxy-1H-indole was prepared from the appropriate starting material.

MS: M=512.1 (API+)

$^1$H-NMR(400 MHz, CDCl$_3$): δ (ppm)=1.57 (m, 2H), 1.98 (m, 2H), 2.25 (s, 3H), 2.58 (t, 2H), 4.41 (t, 2H), 5.02 (s, 2H), 6.77 (m, 2H), 6.99 (d, 1H), 7.14 (m, 2H), 7.38 (d, 1H), 7.51 (d, 1H), 7.52 (s, 1H), 7.70 (s, 1H), 7.73 (s, 1H), 9.44 (br, 1H)

EXAMPLE 7

5-Fluoro-2-{4-[3-methyl-4-(4-[1,2,3]triazol-1-yl-butyl)-phenoxymethyl]-oxazol-2-yl}-1H-indole In an analogous manner as described for example 15-Fluoro-2-{4-[3-methyl-4-(4-[1,2,3]triazol-1-yl-butyl)-phenoxymethyl]-oxazol-2-yl}-1H-indole was prepared from the appropriate starting material.

MS: M=446.1 (API+)

$^1$H-NMR(400 MHz, CDCl$_3$): δ (ppm)=1.57 (m, 2H), 1.97 (m, 2H), 2.24 (s, 3H), 2.58 (t, 2H), 4.40 (t, 2H), 5.01 (s, 2H), 6.76 (m, 2H), 7.00 (m, 2H), 7.08 (s, 1H), 7.31 (m, 2H), 7.50 (s, 1H), 7.70 (s, 1H), 7.72 (s, 1H), 9.24 (br, 1H)

EXAMPLE 8

6-Fluoro-2-{4-[3-methyl-4-(4-[1,2,3]triazol-1-yl-butyl)-phenoxymethyl]-oxazol-2-yl}-1H-indole In an analogous manner as described for example 16-Fluoro-2-{4-[3-methyl-4-(4-[1,2,3]triazol-1-yl-butyl)-phenoxymethyl]-oxazol-2-yl}-1H-indole was prepared from the appropriate starting material.

MS: M=446.1 (API+)

$^1$H-NMR(400 MHz, DMSO-d$_6$): 6 (ppm)=1.43 (m, 2H), 1.86 (m, 2H), 2.21 (s, 3H), 2.52 (t, 2H), 4.41 (t, 2H), 5.01 (s, 2H), 6.81 (m, 2H), 6.95 (m, 1H), 7.01 (d, 1H), 7.10 (s, 1H), 7.15 (d, 1H), 7.65 (m, 1H), 7.71 (s, 1H), 8.12 (s, 1H), 8.28 (s, 1H), 12.18 (br, 1H)

EXAMPLE 9

6-Chloro-2-{4-[3-methyl-4-(4-[1,2,3]triazol-1-yl-butyl)-phenoxymethyl]-oxazol-2-yl}-1H-indole In an analogous manner as described for example 16-Chloro-2-{4-[3-methyl-4-(4-[1,2,3]triazol-1-yl-butyl)-phenoxymethyl]-oxazol-2-yl}-1H-indole was prepared from the appropriate starting material.

MS: M=462.1 (API+)

$^1$H-NMR(400 MHz, CDCl$_3$): δ (ppm)=1.58 (m, 2H), 1.98 (m, 2H), 2.25 (s, 3H), 2.59 (t, 2H), 4.41 (t, 2H), 5.02 (s, 2H), 6.78 (m, 2H), 7.00 (d, 1H), 7.11 (m, 2H), 7.40 (s, 1H), 0.50 (s, 1H), 7.57 (d, 1H), 7.70 (s, 1H), 7.72 (s, 1H), 9.07 (br, 1H)

EXAMPLE 10

5-Chloro-2-{4-[4-(2-[1,2,3]triazol-1-yl-ethoxymethyl)-phenoxymethyl]-oxazol-2-yl}-1H-indole In an analogous manner as described for example 15-Chloro-2-{4-[4-(2-[1,2,3]triazol-1-yl-ethoxymethyl)-phenoxymethyl]-oxazol-2-yl}-1H-indole was prepared from the appropriate starting material.

MS: M=450.4 (ESI+)

$^1$H-NMR(400 MHz, DMSO-d$_6$): δ (ppm)=3.80 (t, 2H), 4.40 (s, 2H), 4.58 (t, 2H), 5.07 (s, 2H), 7.01 (d, 2H), 7.07 (s, 1H), 7.19 (m, 3H), 7.43 (d, 1H), 7.69 (s, 1H), 7.72 (s, 1H), 8.08 (s, 1H), 8.34 (s, 1H), 12.30 (br, 1H)

EXAMPLE 11

5-Fluoro-2-{4-[4-(2-[1,2,3]triazol-1-yl-ethoxymethyl)-phenoxymethyl]-oxazol-2-yl}-1H-indole In an analogous manner as described for example 15-Fluoro-2-{4-[4-(2-[1,2,3]triazol-1-yl-ethoxymethyl)-phenoxymethyl]-oxazol-2-yl}-1H-indole was prepared from the appropriate starting material.

MS: M=434.4 (ESI+)

$^1$H-NMR(400 MHz, DMSO-d$_6$; δ (ppm)=3.80 (t, 2H), 4.40 (s, 2H), 4.58 (t, 2H), 5.07 (s, 2H), 7.05 (m, 4H), 7.19 (m, 2H), 7.40 (m, 2H), 7.72 (s, 1H), 8.08 (s, 1H), 8.33 (s, 1H), 12.20 (br, 1H)

EXAMPLE 12

5-Chloro-2-{4-[4-(2-[1,2,3]triazol-1-yl-ethanesulfinylmethyl)-phenoxymethyl]-oxazol-2-yl}-1H-indole In an analogous manner as described for example 15-Chloro-2-{4-[4-(2-[1,2,3]triazol-1-yl-ethanesulfinylmethyl)-phenoxymethyl]-oxazol-2-yl}-1H-indole was prepared from the appropriate starting material.

MS: M=482.2 (ESI+)

$^1$H-NMR(400 MHz, DMSO-d$_6$): δ (ppm)=3.13 (m, 1H A-part of an AB-system), 3.33 (m, 1H, B-part of an AB-system), 3.96 (d, 1H, A-part of an AB-system), 4.13 (d, 1H, B-part of an AB-system), 4.79 (t, 2H), 5.08 (s, 2H), 7.08 (m, 3H), 7.23 (m, 3H), 7.43 (d, 1H), 7.69 (s, 1H), 7.75 (s, 1H), 8.17 (s, 1H), 8.35 (s, 1H), 12.30 (br, 1H)

EXAMPLE 13

5-Fluoro-2-{4-[4-(2-[1,2,3]triazol-1-yl-ethanesulfinylmethyl)-phenoxymethyl]-oxazol-2-yl}-1H-indole In an analogous manner as described for example 15-Fluoro-2-{4-[4-(2-[1,2,3]triazol-1-yl-ethanesulfinylmethyl)-phenoxymethyl]-oxazol-2-yl}-1H-indole was prepared from the appropriate starting material.

MS: M=466.2 (ESI+)

$^1$H-NMR(400 MHz DMSO-d$_6$): δ (ppm)=3.15 (m, 1H, A-part of an AB-system), 3.34 (m, 1H, B-part of an AB-system), 3.96 (d, 1H, A-part of an AB-System), 4.14 (d, 1H, B-part of an AB-system), 4.79 (t, 2H), 5.08 (s, 2H), 7.07 (m, 4H), 7.26 (d, 2H), 7.41 (m, 2H), 7.75 (s, 1H), 8.17 (s, 1H), 8.34 (s, 1H), 12.20 (br, 1H)

EXAMPLE 14

2-{4-[3-(3-[1,2,3]Triazol-1-yl-propyl)-phenoxymethyl]-oxazol-2-yl}-5-trifluoromethoxy-1H-indole In an analogous manner as described for example 1 2-{4-[3-(3-[1,2,3]Triazol-1-yl-propyl)-phenoxymethyl]-oxazol-2-yl}-5-trifluoromethoxy-1H-indole was prepared from the appropriate starting material.

MS: M=484.1 (API+)

$^1$H-NMR(400 MHz, CDCl$_3$): δ (ppm)=2.26 (m, 2H), 2.63 (t, 2H), 4.39 (t, 2H), 5.06 (s, 2H), 6.81 (d, 1H), 6.86 (m, 2H), 7.14 (m, 2H), 7.22 (s, 1H), 7.40 (d, 1H), 7.52 (s, 2H), 7.72 (s, 1H), 7.77 (s, 1H), 9.50 (br, 1H)

EXAMPLE 15

5-Fluoro-2-{4-[3-(3-[1,2,3]triazol-1-yl-propyl)-phenoxymethyl]-oxazol-2-yl}-1H-indole In an analogous manner as described for example 15-Fluoro-2-{4-[3-(3-[1,2,3]triazol-1-yl-propyl)-phenoxymethyl]-oxazol-2-yl}-1H-indole was prepared from the appropriate starting material.
MS: M=418.0 (API+)
$^1$H-NMR(400 MHz, CDCl$_3$) δ=2.26 (m, 2H), 2.63 (t, 2H), 4.39 (t, 2H), 5.06 (s, 2H), 6.81 (d, 1H), 6.85-6.87 (m, 2H), 7.03 (t, 1H), 7.09 (s, 1H), 7.23-7.33 (m, 3H), 7.52 (s, 1H), 7.72 (s, 1H), 7.75 (s, 1H), 9.21 (br, 1H)

EXAMPLE 16

6-Chloro-2-{4-[3-(3-[1,2,3]triazol-1-yl-propyl)-phenoxymethyl]-oxazol-2-yl}-1H-indole In an analogous manner as described for example 16-Chloro-2-{4-[3-(3-[1,2,3]triazol-1-yl-propyl)-phenoxymethyl]-oxazol-2-yl}-1H-indole was prepared from the appropriate starting material.
MS: M=434.1 (API+)
$^1$H-NMR(400 MHz, CDCl$_3$): δ (ppm)=2.26 (m, 2H), 2.63 (t, 2H), 4.39 (t, 2H), 5.06 (s, 2H), 6.81 (d, 1H), 6.86 (m, 2H), 7.11 (m, 2H), 7.22 (m, 1H), 7.41 (s, 1H), 7.52 (s, 1H), 7.57 (d, 1H), 7.72 (s, 1H), 7.75 (s, 1H), 9.29 (br, 1H)

EXAMPLE 17

5-Chloro-2-{4-[4-(4-[1,2,3]triazol-1-yl-butyl)-phenoxymethyl]-thiazol-2-yl}-1H-indole In an analogous manner as described for example 15-Chloro-2-{4-[4-(4-[1,2,3]triazol-1-yl-butyl)-phenoxymethyl]-thiazol-2-yl}-1H-indole was prepared from the appropriate starting material.
MS: M=464.1 (API+)
$^1$H-NMR(400 MHz, CDCl$_3$): δ (ppm)=1.55 (m, 2H), 1.87 (m, 2H), 2.53 (t, 2H), 4.32 (t, 2H), 5.12 (s, 2H), 6.84 (m, 3H), 7.00 (m, 2H), 7.13 (m, 1H), 7.21 (m, 2H), 7.42 (s, 1H), 7.53 (s, 1H), 7.62 (s, 1H), 9.20 (br, 1H)

EXAMPLE 18

5-Chloro-2-{4-[4-(2-[1,2,3]triazol-1-yl-ethoxymethyl)-phenoxymethyl]-thiazol-2-yl}-1H-indole In an analogous manner as described for example 15-Chloro-2-{4-[4-(2-[1,2,3]triazol-1-yl-ethoxymethyl)-phenoxymethyl]-thiazol-2-yl}-1H-indole was prepared from the appropriate starting material.
MS: M=466.0 (API+)
$^1$H-NMR(400 MHz, DMSO-d$_6$): δ (ppm)=3.80 (t, 2H), 4.41 (s, 2H), 4.58 (t, 2H), 5.21 (s, 2H), 7.03 (m, 3H), 7.19 (m, 3H), 7.43 (d, 1H), 7.64 (d, 1H), 7.72 (s, 1H), 7.79 (s, 1H), 8.09 (s, 1H), 12.17 (br, 1H)

EXAMPLE 19

5-Chloro-2-{4-[4-(2-[1,2,3]triazol-1-yl-ethanesulfinylmethyl)-phenoxymethyl]-thiazol-2-yl}-1H-indole In an analogous manner as described for example 15-Chloro-2-{4-[4-(2-[1,2,3]triazol-1-yl-ethanesulfinylmethyl)-phenoxymethyl]-thiazol-2-yl}-1H-indole was prepared from the appropriate starting material.
MS: M=498.0 (ESI+)
$^1$H-NMR(400 MHz, DMSO-d$_6$): δ (ppm)=3.13 (m, 1H, A-part of an AB-system), 3.34 (m, 1H, B-part of an AB-system), 3.96 (d, 1H, A-part of an AB-System), 4.14 (d, 1H, B-part of an AB-system), 4.79 (t, 2H), 5.23 (s, 2H), 7.07 (m, 3H), 7.22 (d, 2H), 7.44 (m, 2H), 7.64 (s, 1H), 7.75 (s, 1H), 7.81 (s, 1H), 8.17 (s, 1H), 12.17 (br, 1H)

EXAMPLE 20

2-{4-[4-(4-[1,2,3]Triazol-1-yl-butyl)-benzenesulfonylmethyl]-oxazol-2-yl}-5-trifluoromethoxy-1H-indole To a solution of 1-but-3-enyl-1H-[1,2,3]triazole (69 mg, 0.56 mmol) in THF (5 ml) 9-borabicyclo[3.3.1]nonane (0.5 M in THF, 2.46 ml, 1.23 mmol) was added dropwise at 0° C. and stirring continued for 2 h. This mixture was then added to a solution of 2-[4-(4-bromo-benzenesulfonylmethyl)-oxazol-2-yl]-5-trifluoromethoxy-1H-indole (0.28 g, 0.56 mmol), Pd(dppf)Cl$_2$ (49 mg, 0.06 mmol) and aqueous cesium carbonate (0.56 ml, 3M) in DMF (5 ml) and stirred for 3 h at 70° C. Water (10 ml) was added and the mixture extracted with ethyl acetate (3×20 ml). The combined organic layers were washed with water and brine, dried over sodium sulfate and concentrated. The crude product was purified on silica gel (ethyl acetate) to yield 2-{4-[4-(4-[1,2,3]Triazol-1-yl-butyl)-benzenesulfonylmethyl]-oxazol-2-yl}-5-trifluoromethoxy-1H-indole as light yellow solid. Yield 24 mg (8%)
MS: M=546.1 (API+)
$^1$H-NMR(400 MHz, [D$_6$]-DMSO): δ=1.52 (m, 2H), 1.81 (m, 2H), 2.69 (t, 2H), 4.38 (t, 2H), 4.70 (s, 2H), 7.09 (s, 1H), 7.18 (d, 1H), 7.43 (d, 2H), 7.51 (d, 1H), 7.63 (s, 1H), 7.70 (s, 1H), 7.74 (d, 2H), 8.09 (s, 1H), 8.12 (s, 1H)

EXAMPLE 21

5-Fluoro-2-{4-[4-(4-[1,2,3]triazol-1-yl-butyl)-benzenesulfonylmethyl]-oxazol-2-yl}-1H-indole In an analogous manner as described for example 20 5-Fluoro-2-{4-[4-(4-[1,2,3]triazol-1-yl-butyl)-benzenesulfonylmethyl]-oxazol-2-yl}-1H-indole was prepared from the appropriate starting material.
MS: M=480.1 (API+)
$^1$H-NMR(400 MHz, CDCl$_3$): δ (ppm)=1.62 (q, 2H), 1.90 (q, 2H), 2.70 (t, 2H), 4.35 (t, 2H), 4.39 (s, 2H), 7.02 (m, 2H), 7.28 (m, 4H), 7.48 (s, 1H), 7.67 (s, 1H), 7.70 (s, 1H), 7.73 (s, 1H), 7.75 (s,1H), 9.19 (br, 1H)

EXAMPLE 22

[4-(4-[1,2,3]Triazol-1-yl-butyl)-phenyl]-[2-(5-trifluoromethoxy-1H-indol-2-yl)-oxazol-4-ylmethyl]-amine To a solution of [4-(4-[1,2,3]Triazol-1-yl-butyl)-phenyl]-carbamic acid tert-butyl ester (0.297 g, 0.94 mmol) in N,N-dimethyl formamide (5 ml) sodium hydride (0.050 g, 2.1 mmol) was added and the mixture stirred for 30 min at r.t. To this mixture a solution of 2-(4-chloromethyl-oxazol-2-yl)-5-trifluoromethoxy-1H-indole 0.3 g, 0.94 mmol) in N,N-dimethyl formamide (5 ml) was added and stirring continued for 16 h. The mixture was then poured on water (25 ml) and extracted with ethyl acetate (3×25 ml). The combined organic extracts was washed with water, brine and dried over sodium sulfate. After concentration in vacuo the crude product was purified on silica gel (iso-hexanes/ethyl acetate 1:2) to yield [4-(4-[1,2,3]Triazol-1-yl-butyl)-phenyl]-[2-(5-trifluoromethoxy-1H-indol-2-yl)-oxazol-4-ylmethyl]-carbamic acid tert-butyl ester as light yellow solid.

[4-(4-[1,2,3]Triazol-1-yl-butyl)-phenyl]-[2-(5-trifluoromethoxy-1H-indol-2-yl)-oxazol-4-ylmethyl]-carbamic acid tert-butyl ester (0.31 g, 0.52 mmol) was stirred in a mixture of dichloro methane and trifluoro acetic acid (1:1, 10 ml) for 3 h. After concentration the crude product was purified on silica gel (ethyl acetate) yielding [4-(4-[1,2,3]triazol-1-yl-butyl)-phenyl]-[2-(5-trifluoromethoxy-1H-indol-2-yl)-oxazol-4-ylmethyl]-amine as light yellow solid.

MS: M=497.1 (API+)

$^1$H-NMR(400 MHz, CDCl$_3$): δ=1.59 (m, 2H), 1.92 (m, 2H), 2.54 (t, 2H), 4.30 (s, 2H), 4.39 (t, 2H), 6.62 (d, 2H), 6.96 (d, 2H), 7.10 (s, 1H), 7.13 (d, 1H), 7.36 (d, 1H), 7.48 (s, 1H), 7.51 (s, 1H), 7.59 (s, 1H), 7.69 (s, 1H), 9.41 (br, 1H)

EXAMPLE 23

[2-(6-Fluoro-1H-indol-2-yl)-oxazol-4-ylmethyl]-[4-(4-[1,2,3]triazol-1-yl-butyl)-phenyl]-amine In an analogous manner as described for example 22 [2-(6-Fluoro-1H-indol-2-yl)-oxazol-4-ylmethyl]-[4-(4-[1,2,3]triazol-1-yl-butyl)-phenyl]-amine was prepared from the appropriate starting material.

MS: M=431.1 (API+)

$^1$H-NMR(400 MHz, CDCl$_3$): δ (ppm)=1.59 (m, 2H), 1.92 (m, 2H), 2.54 (t, 2H), 4.16 (br,1H), 4.30 (s, 2H), 4.37 (t, 2H), 6.62 (d, 2H), 6.96 (m, 3H), 7.07 (m, 2H), 7.48 (s, 1H), 7.57 (m, 2H),

EXAMPLE 24

[2-(5-Fluoro-1H-indol-2-yl)-oxazol-4-ylmethyl]-[4-(4-[1,2,3]triazol-1-yl-butyl)-phenyl]-amine In an analogous manner as described for example 22 [2-(5-Fluoro-1H-indol-2-yl)-oxazol-4-ylmethyl]-[4-(4-[1,2,3]triazol-1-yl-butyl)-phenyl]-amine was prepared from the appropriate starting material.

MS: M=431.2 (API+)

$^1$H-NMR(400 MHz, CDCl$_3$) δ (ppm)=1.59 (m, 2H), 1.92 (m, 2H), 2.54 (t, 2H), 4.15 (br, 1H), 4.30 (s, 2H), 4.37 (t, 2H), 6.62 (d, 2H), 7.01 (m, 4H), 7.31 (m, 2H), 7.48 (s, 1H), 7.58 (s, 1H), 7.68 (s, 1H), 9.11 (br, 1H)

EXAMPLE 25

[2-(6-Chloro-1H-indol-2-yl)-oxazol-4-ylmethyl]-[4-(4-[1,2,3]triazol-1-yl-butyl)-phenyl]-amine In an analogous manner as described for example 22 [2-(6-Chloro-1H-indol-2-yl)-oxazol-4-ylmethyl]-[4-(4-[1,2,3]triazol-1-yl-butyl)-phenyl]-amine was prepared from the appropriate starting material.

MS: M=447.1 (API+)

$^1$H-NMR(400 MHz, CDCl$_3$): δ (ppm)=1.59 (m, 2H), 1.92 (m, 2H), 2.54 (t, 2H), 4.30 (s, 2H), 4.37 (t, 2H), 6.62 (d, 1H), 6.97 (d, 2H), 7.07 (d, 2H), 7.11 (m, 1H), 7.39 (s, 1H), 7.48 (s, 1H), 7.55 (s, 1H), 7.57 (s, 1H), 7.68 (s, 1H), 9.53 (br, 1H)

EXAMPLE 26

[2-(5-Chloro-1H-indol-2-yl)-oxazol-4-ylmethyl]-[4-(4-[1,2,3]triazol-1-yl-butyl)-phenyl]-amine In an analogous manner as described for example 22 [2-(5-Chloro-1H-indol-2-yl)-oxazol-4-ylmethyl]-[4-(4-[1,2,3]triazol-1-yl-butyl)-phenyl]-amine was prepared from the appropriate starting material.

MS: M=447.1 (API+)

$^1$H-NMR(400 MHz, CDCl$_3$): δ (ppm)=1.59 (m, 2H), 1.92 (m, 2H), 2.54 (t, 2H), 4.22 (br, 1H), 4.30 (s, 2H), 4.37 (t, 2H), 6.61 (d, 2H), 6.96 (d, 2H), 7.03 (d, 1H), 7.26 (m, 2H), 7.48 (s, 1H), 7.58 (s, 1H), 7.63 (m, 1H), 7.68 (s, 1H), 9.29 (br, 1H)

EXAMPLE 27

[2-(5-Fluoro-1H-indol-2-yl)-oxazol-4-ylmethyl]-[3-methyl-4-(4-[1,2,3]triazol-1-yl-butyl)-phenyl]-amine In an analogous manner as described for example 22 [2-(5-Fluoro-1H-indol-2-yl)-oxazol-4-ylmethyl]-[3-methyl-4-(4-[1,2,3]triazol-1-yl-butyl)-phenyl]-amine was prepared from the appropriate starting material.

MS: M=445.2 (API+)

$^1$H-NMR(400 MHz, CDCl$_3$): δ (ppm)=1.55 (m, 2H), 1.97 (m, 2H), 2.20 (s, 3H), 2.54 (t, 2H), 4.06 (br, 1H), 4.29 (s, 2H), 4.39 (t, 2H), 6.48 (m, 2H), 6.91 (d, 1H), 7.04 (m, 2H), 7.31 (m, 2H), 7.49 (s, 1H), 7.58 (s, 1H), 7.69 (s, 1H), 9.04 (br, 1H)

EXAMPLE 28

[2-(6-Fluoro-1H-indol-2-yl)-oxazol-4-ylmethyl]-[3-methyl-4-(4-[1,2,3]triazol-1-yl-butyl)-phenyl]-amine In an analogous manner as described for example 22 [2-(6-Fluoro-1H-indol-2-yl)-oxazol-4-ylmethyl]-[3-methyl-4-(4-[1,2,3]triazol-1-yl-butyl)-phenyl]-amine was prepared from the appropriate starting material.

MS: M=445.1 (API+)

$^1$H-NMR(400 MHz, CDCl$_3$): δ (ppm)=1.55 (m, 2H), 1.96 (m, 2H), 2.20 (s, 3H), 2.54 (t, 2H), 4.08 (br, 1H), 4.29 (s, 2H), 4.39 (t, 2H), 6.48 (m, 2H), 6.91 (m, 2H), 7.06 (m, 2H), 7.49 (s, 1H), 7.57 (m, 2H), 7.69 (s, 1H), 9.11 (br, 1H)

EXAMPLE 29

[2-(5-Chloro-1H-indol-2-yl)-oxazol-4-ylmethyl]-[3-methyl-4-(4-[1,2,3]triazol-1-yl-butyl)-phenyl]-amine In an analogous manner as described for example 22 [2-(5-Chloro-1H-indol-2-yl)-oxazol-4-ylmethyl]-[3-methyl-4-(4-[1,2,3]triazol-1-yl-butyl)-phenyl]-amine was prepared from the appropriate starting material.

MS: M=461.1 (API+)

$^1$H-NMR(400 MHz, CDCl$_3$): δ (ppm)=1.55 (m, 2H), 1.96 (m, 2H), 2.20 (s, 3H), 2.54 (t, 2H), 4.07 (br, 1H), 4.29 (s, 2H), 4.39 (t, 2H), 6.48 (m, 2H), 6.90 (d, 1H), 7.03 (d, 1H), 7.22 (m, 1H), 7.31 (d, 1H), 7.49 (s, 1H), 7.58 (s, 1H), 7.63 (s, 1H), 7.69 (s, 1H), 9.13 (br, 1H)

EXAMPLE 30

[2-(5-Chloro-1H-indol-2-yl)-oxazol-4-ylmethyl]-[4-(4-[1,2,3]triazol-1-yl-butyl)-3-trifluoromethyl-phenyl]-amine In an analogous manner as described for example 22 [2-(5-Chloro-1H-indol-2-yl)-oxazol-4-ylmethyl]-[4-(4-[1,2,3]triazol-1-yl-butyl)-3-trifluoromethyl-phenyl]-amine was prepared from the appropriate starting material.

MS: M=515.1 (API+)

$^1$H-NMR(400 MHz, CDCl$_3$): δ=1.59 (m, 2H), 1.97 (m, 2H), 2.69 (t, 2H), 4.31 (s, 2H), 4.40 (t, 2H), 6.75 (d, 1H), 6.90 (d, 2H), 7.05 (s, 1H), 7.06 (d, 1H), 7.22 (d, 1H), 7.32 (d, 1H), 7.51 (s, 1H), 7.60 (s, 1H), 7.63 (s, 1H), 7.70 (s, 1H), 9.08 (br, 1H)

EXAMPLE 31

[2-(5-Fluoro-1H-indol-2-yl)-oxazol-4-ylmethyl]-[4-(4-[1,2,3]triazol-1-yl-butyl)-3-trifluoromethyl-phenyl]-amine In an analogous manner as described for example 22 [2-(5-Fluoro-1H-indol-2-yl)-oxazol-4-ylmethyl]-[4-(4-[1,2,3]triazol-1-yl-butyl)-3-trifluoromethyl-phenyl]-amine was prepared from the appropriate starting material.

MS: M=499.1 (API+)

$^1$H-NMR(400 MHz, CDCl$_3$): δ (ppm)=1.52 (m, 2H), 1.91 (m, 2H), 2.62 (t, 2H), 4.24 (s, 2H), 4.33 (t, 2H), 6.68 (m, 1H), 6.84 (d, 1H), 6.97 (m, 3H), 7.25 (m, 2H), 7.44 (s, 1H), 7.53 (s, 1H), 7.63 (s, 1H), 8.95 (br, 1H)

EXAMPLE 32

[2-(5-Fluoro-1H-indol-2-yl)-oxazol-4-ylmethyl]-[3-fluoro-4-(4-[1,2,3]triazol-1-yl-butyl)-phenyl]-amine In an analogous manner as described for example 22 [2-(5-Fluoro-1H-indol-2-yl)-oxazol-4-ylmethyl]-[3-fluoro-4-(4-[1,2,3]triazol-1-yl-butyl)-phenyl]-amine was prepared from the appropriate starting material.

MS: M=449.1 (API+)

$^1$H-NMR(400 MHz, CDCl$_3$): δ (ppm)=1.59 (m, 2H), 1.93 (m, 2H), 2.57 (t, 2H), 4.23 (br, 1H), 4.28 (s, 2H), 4.39 (t, 2H), 6.38 (m, 2H), 3.92 (m, 1H), 7.05 (m, 2H), 7.31 (m, 2H), 7.50 (s, 1H), 7.59 (s, 1H), 7.69 (s, 1H), 9.01 (br, 1H)

EXAMPLE 33

[2-(5-Chloro-1H-indol-2-yl)-oxazol-4-ylmethyl]-[3-fluoro-4-(4-[1,2,3]triazol-1-yl-butyl)-phenyl]-amine In an analogous manner as described for example 22 [2-(5-Chloro-1H-indol-2-yl)-oxazol-4-ylmethyl]-[3-fluoro-4-(4-[1,2,3]triazol-1-yl-butyl)-phenyl]-amine was prepared from the appropriate starting material.

MS: M=465.1 (API+)

$^1$H-NMR(400 MHz, CDCl$_3$): δ (ppm)=1.59 (m, 2H), 1.93 (m, 2H), 2.57 (t, 2H), 4.22 (br, 1H), 4.28 (s, 2H), 4.39 (t, 2H), 6.38 (m, 2H), 6.92 (m, 1H), 7.05 (s, 1H), 7.23 (d, 1H), 7.33 (d, 1H), 7.50 (s, 1H), 7.60 (s, 1H), 7.64 (s, 1H), 7.69 (s, 1H), 9.03 (br, 1H)

EXAMPLE 34

[2-(5-Fluoro-1H-indol-2-yl)-oxazol-4-ylmethyl]-[2-fluoro-4-(4-[1,2,3]triazol-1-yl-butyl)-phenyl]-amine In an analogous manner as described for example 22 [2-(5-Fluoro-1H-indol-2-yl)-oxazol-4-ylmethyl]-[2-fluoro-4-(4-[1,2,3]triazol-1-yl-butyl)-phenyl]-amine was prepared from the appropriate starting material.

MS: M=449.1 (API+)

$^1$H-NMR(400 MHz, CDCl$_3$): δ (ppm)=1.59 (m, 2H), 1.92 (m, 2H), 2.54 (t, 2H), 4.34 (s, 2H), 4.38 (t, 2H), 6.68 (m, 1H), 6.78 (m, 2H), 7.03 (m, 2H), 7.31 (m, 2H), 7.49 (s, 1H), 7.59 (s, 1H), 7.69 (s, 1H), 9.00 (br, 1H)

EXAMPLE 35

[2-(5-Chloro-1H-indol-2-yl)-oxazol-4-ylmethyl]-[2-fluoro-4-(4-[1,2,3]triazol-1-yl-butyl)-phenyl]-amine In an analogous manner as described for example 22 [2-(5-Chloro-1H-indol-2-yl)-oxazol-4-ylmethyl]-[2-fluoro-4-(4-[1,2,3]triazol-1-yl-butyl)-phenyl]-amine was prepared from the appropriate starting material.

MS: M=465.1 (API+)

$^1$H-NMR(400 MHz, CDCl$_3$): δ (ppm)=1.59 (m, 2H), 1.92 (m, 2H), 1.54 (t, 2H), 4.33 (s, 2H), 4.35 (br, 1H), 4.38 (t, 2H), 6.67 (m, 1H), 7.04 (s, 1H), 7.22 (d, 2H), 7.33 (d, 2H), 7.49 (s, 1H), 7.59 (s, 1H), 7.64 (s, 1H), 7.69 (s, 1H), 9.07 (br, 1H)

EXAMPLE 36

[2-(6-Chloro-1H-indol-2-yl)-oxazol-4-ylmethyl]-[3-(3-[1,2,3]triazol-1-yl-propyl)-phenyl]-amine In an analogous manner as described for example 22 [2-(6-Chloro-1H-indol-2-yl)-oxazol-4-ylmethyl]-[3-(3-[1,2,3]triazol-1-yl-propyl)-phenyl]-amine was prepared from the appropriate starting material.

MS: M=433.0 (API+)

$^1$H-NMR(400 MHz, CDCl): δ (ppm)=2.23 (m, 2H), 2.56 (t, 2H), 4.31 (s, 2H), 4.37 (t, 2H), 6.50 (s, 1H), 6.56 (m, 2H), 7.10 (m, 3H), 7.41 (s, 1H), 7.50 (s, 1H), 7.56 (d, 1H), 7.60 (s, 1H), 7.70 (s, 1H), 9.63 (br, 1H)

EXAMPLE 37

[2-(5-Fluoro-1H-indol-2-yl)-oxazol-4-ylmethyl]-[3-(3-[1,2,3]triazol-1-yl-propyl)-phenyl]-amine In an analogous manner as described for example 22 [2-(5-Fluoro-1H-indol-2-yl)-oxazol-4-ylmethyl]-[3-(3-[1,2,3]triazol-1-yl-propyl)-phenyl]-amine was prepared from the appropriate starting material.

MS: M=417.1 (API+)

$^1$H-NMR(400 MHz, CDCl$_3$): δ (ppm)=2.23 (m, 2H), 2.56 (t, 2H), 4.28 (br, 1H), 4.31 (s, 2H), 4.37 (t, 2H), 6.50 (s, 1H), 6.56 (m, 2H), 7.03 (m, 2H), 7.13 (t, 1H), 7.31 (m, 2H), 7.50 (s, 1H), 7.60 (s, 1H), 7.70 (s, 1H), 9.28 (br, 1H)

EXAMPLE 38

[2-(5-Fluoro-1H-indol-2-yl)-oxazol-4-ylmethyl]-[6-(4-[1,2,3]triazol-1-yl-butyl)-pyridin-3-yl]-amine In an analogous manner as described for example 22 [2-(5-Fluoro-1H-indol-2-yl)-oxazol-4-ylmethyl]-[6-(4-[1,2,3]triazol-1-yl-butyl)-pyridin-3-yl]-amine was prepared from the appropriate starting material.

MS: M=432.1 (API+)

$^1$H-NMR(400 MHz, CDCl$_3$): δ (ppm)=1.72 (m, 2H), 1.95 (m, 2H), 2.72 (t, 2H), 4.19 (br, 1H), 4.31 (s, 2H), 4.39 (t, 2H), 6.93 (m, 2H), 7.05 (m, 2H), 7.31 (m, 2H), 7.51 (s, 1H), 7.60 (s, 1H), 7.68 (s, 1H), 8.06 (d, 1H), 9.15 (br, 1H)

EXAMPLE 39

[2-(5-Fluoro-1H-indol-2-yl)-oxazol-4-ylmethyl]-[5-(4-[1,2,3]triazol-1-yl-butyl)-pyridin-2-yl]-amine In an analogous manner as described for example 22 [2-(5-Fluoro-1H-indol-2-yl)-oxazol-4-ylmethyl]-[5-(4-[1,2,3]triazol-1-yl-butyl)-pyridin-2-yl]-amine was prepared from the appropriate starting material.

MS: M=432.1 (API+)

$^1$H-NMR(400 MHz, CDCl$_3$): δ (ppm)=1.58 (m, 2H), 1.93 (m, 2H), 2.51 (t, 2H), 4.39 (t, 2H), 4.49 (d, 2H), 5.05 (br, t, 1H), 6.42 (d, 1H), 7.02 (m, 2H), 7.22 (m, 1H), 7.30 (m, 2H), 7.50 (s, 1H), 7.60 (s, 1H), 7.70 (s, 1H), 7.93 (d, 1H), 9.31 (br, 1H)

EXAMPLE 40

5-Fluoro-2-{4-[3-methyl-4-(2-[1,2,3]triazol-1-yl-ethoxymethyl)-phenoxymethyl]-oxazol-2-yl}-1H-indole In an analogous manner as described for example 15-Fluoro-2-{4-[3-methyl-4-(2-[1,2,3]triazol-1-yl-ethoxymethyl)-phenoxymethyl]-oxazol-2-yl}-1H-indole was prepared from the appropriate starting material.

MS: M=448.2 (API+)

$^1$H-NMR(400 MHz, DMSO-d$_6$): δ (ppm)=2.13 (s, 3H), 3.81 (t, 2H), 4.39 (s, 2H), 4.58 (t, 2H), 5.04 (s, 2H), 6.83 (m, 2H), 7.07 (m, 2H), 7.13 (m, 1H), 7.41 (m, 2H), 7.71 (s, 1H), 8.06 (s, 1H), 8.31 (s, 1H), 12.19 (br, 1H)

EXAMPLE 41

5-Fluoro-2-{4-[3-methyl-4-(2-[1,2,3]triazol-1-yl-ethanesulfinylmethyl)-phenoxymethyl]-oxazol-2-yl}-1H-indole In an analogous manner as described for example 15-Fluoro-2-{4-[3-methyl-4-(2-[1,2,3]triazol-1-yl-ethanesulfinylmethyl)-phenoxymethyl]-oxazol-2-yl}-1H-indole was prepared from the appropriate starting material.

MS: M=480.3 (API+)

$^1$H-NMR(400 MHz, DMSO-d$_6$): δ (ppm)=2.30 (s, 3H), 3.27 (m, 1H, A-part of an AB-system), 3.43 (m, 1H, B-part of an AB-system), 4.02 (d, 1H, A-part of an AB-System), 4.16 (d, 1H, B-part of an AB-system), 4.82 (m, 2H), 5.07 (s, 2H), 6.91 (m, 2H), 7.07 (m, 2H), 7.18 (d, 1H), 7.41 (m, 2H), 7.75 (s, 1H), 8.18 (s, 1H), 8.33 (s, 1H), 12.20 (br, 1H)

EXAMPLE 42

5-Fluoro-2-{4-[3-methyl-4-(2-[1,2,3]triazol-1-yl-ethanesulfonylmethyl)-phenoxymethyl]-oxazol-2-yl}-1H-indole In an analogous manner as described for example 15-Fluoro-2-{4-[3-methyl-4-(2-[1,2,3]triazol-1-yl-ethanesulfonylmethyl)-phenoxymethyl]-oxazol-2-yl}-1H-indole was prepared from the appropriate starting material.

MS: M=496.3 (API+)

$^1$H-NMR(400 MHz, DMSO-d$_6$): δ (ppm)=2.35 (s, 3H), 3.83 (t, 2H), 4.43 (s, 2H), 4.86 (t, 2H), 5.08 (s, 2H), 6.94 (m, 2H), 7.07 (m, 2H), 7.23 (d, 1H), 7.41 (m, 2H), 7.76 (s, 1H), 8.21 (s, 1H), 8.34 (s, 1H), 12.20 (br, 1H)

Unless stated to the contrary, all compounds in the examples were prepared and characterized as described. All ranges recited herein encompass all combinations and subcombinations included within that range limit. All patents and publications cited herein are hereby incorporated by reference in their entirety for any purpose.

The invention claimed is:

1. A compound of formula I or pharmaceutically acceptable salts thereof wherein formula I is:

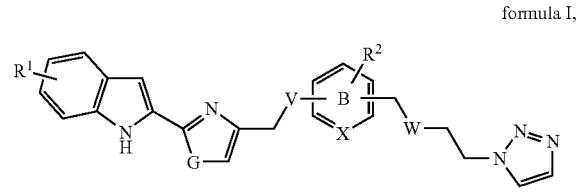

formula I, wherein:

R$^1$ is selected from the group consisting of:
(a) hydrogen,
(b) halogen,
(c) —O-alkyl, wherein the alkyl group is optionally substituted with one or more halogens
(d) —S-alkyl, wherein the alkyl group is optionally substituted with one or more halogens, and
(e) alkyl, wherein the alkyl is optionally substituted with one or more halogens;

R$^2$ is selected from the group consisting of:
(a) hydrogen,
(b) halogen,
(c) alkyl, wherein the alkyl is optionally substituted with one or more halogens, and
(d) —O-alkyl; wherein the alkyl group is optionally substituted with one or more halogens;

G is selected from the group consisting of: —O— and —S—;

V is selected from the group consisting of: —O—, —NH—, —S—, —S(O)—, and —S(O)$_2$—;

W is selected from the group consisting of: a single bond, —CH$_2$—, —O—, —S—, —S(O)—, and —S(O)$_2$—;

X is selected from the group consisting of: =CH— and =N—; and ring B is selected from the group consisting of:
(a) 1,4-phenylene,
(b) 1,3-phenylene,
(c) 2,5-pyridindiyl, and
(d) 3,6-pyridindiyl.

2. The compounds according to claim 1, wherein V is selected from the group consisting of: O—, —NH—, and —S(O)$_2$—.

3. The compounds according to claim 1, wherein V is selected from the group consisting of: —O— and —NH—.

4. The compounds according to claim 1, wherein G is —O— and V is selected from the group consisting of: —O— and —NH—.

5. The compounds according to claim 1, wherein:
   R$^1$ is selected from the group consisting of:
      (a) hydrogen,
      (b) halogen, and
      (c) —O-alkyl; wherein said alkyl group is optionally substituted one or more times by fluorine;
   R$^2$ is selected from the group consisting of: hydrogen and alkyl; and
   G is —O—.

6. The compounds according to claim 1, wherein X is =CH— and ring B is 1,4-phenylene.

7. A compound according to claim 1 selected from the group consisting of:
   2-{4-[4-(4-[1,2,3]Triazol-1-yl-butyl)-phenoxymethyl]-oxazol-2-yl}-5-trifluoromethoxy-1H-indole;
   5-Chloro-2-{4-[4-(4-[1,2,3]triazol-1-yl-butyl)-phenoxymethyl]-oxazol-2-yl}-1H-indole;
   5-Fluoro-2-{4-[4-(4-[1,2,3]triazol-1-yl-butyl)-phenoxymethyl]-oxazol-2-yl}-1H-indole;
   6-Fluoro-2-{4-[4-(4-[1,2,3]triazol-1-yl-butyl)-phenoxymethyl]-oxazol-2-yl}-1H-indole;
   6-Chloro-2-{4-[4-(4-[1,2,3]triazol-1-yl-butyl)-phenoxymethyl]-oxazol-2-yl}-1H-indole;
   2-{4-[3-Methyl-4-(4-[1,2,3]triazol-1-yl-butyl)-phenoxymethyl]-oxazol-2-yl}-5-trifluoromethoxy-1H-indole;
   5-Fluoro-2-{4-[3-methyl-4-(4-[1,2,3]triazol-1-yl-butyl)-phenoxymethyl]-oxazol-2-yl}-1H-indole;
   6-Fluoro-2-{4-[3-methyl-4-(4-[1,2,3]triazol-1-yl-butyl)-phenoxymethyl]-oxazol-2-yl}-1H-indole;
   6-Chloro-2-{4-[3-methyl-4-(4-[1,2,3]triazol-1-yl-butyl)-phenoxymethyl]-oxazol-2-yl}-1H-indole;
   5-Chloro-2-{4-[4-(2-[1,2,3]triazol-1-yl-ethoxymethyl)-phenoxymethyl]-oxazol-2-yl}-1H-indole;
   5-Fluoro-2-{4-[4-(2-[1,2,3]triazol-1-yl-ethoxymethyl)-phenoxymethyl]-oxazol-2-yl}-1H-indole;
   5-Chloro-2-{4-[4-(2-[1,2,3]triazol-1-yl-ethanesulfinylmethyl)-phenoxymethyl]-oxazol-2-yl}-1H-indole;
   5-Fluoro-2-{4-[4-(2-[1,2,3]triazol-1-yl-ethanesulfinylmethyl)-phenoxymethyl]-oxazol-2-yl}-1H-indole;
   2-{4-[3-(3-[1,2,3]Triazol-1-yl-propyl)-phenoxymethyl]-oxazol-2-yl}-5-trifluoromethoxy-1H-indole;
   5-Fluoro-2-{4-[3-(3-[1,2,3]triazol-1-yl-propyl)-phenoxymethyl]-oxazol-2-yl}-1H-indole; and
   6-Chloro-2-{4-[3-(3-[1,2,3]triazol-1-yl-propyl)-phenoxymethyl]-oxazol-2-yl}-1H-indole.

8. A compound according to claim 1 selected from the group consisting of:
   5-Chloro-2-{4-[4-(4-[1,2,3]triazol-1-yl-butyl)-phenoxymethyl]-thiazol-2-yl}-1H-indole;
   5-Chloro-2-{4-[4-(2-[1,2,3]triazol-1-yl-ethoxymethyl)-phenoxymethyl]-thiazol-2-yl}-1H-indole;
   5-Chloro-2-{4-[4-(2-[1,2,3]triazol-1-yl-ethanesulfinylmethyl)-phenoxymethyl]-thiazol-2-yl}-1H-indole;
   2-{4-[4-(4-[1,2,3]Triazol-1-yl-butyl)-benzenesulfonylmethyl]-oxazol-2-yl}-5-trifluoromethoxy-1H-indole;
   5-Fluoro-2-{4-[4-(4-[1,2,3]triazol-1-yl-butyl)-benzenesulfonylmethyl]-oxazol-2-yl}-1H-indole;
   [4-(4-[1,2,3]Triazol-1-yl-butyl)-phenyl]-[2-(5-trifluoromethoxy-1H-indol-2-yl)-oxazol-4-ylmethyl]-amine;
   [2-(6-Fluoro-1H-indol-2-yl)-oxazol-4-ylmethyl]-[4-(4-[1,2,3]triazol-1-yl-butyl)-phenyl]-amine;
   [2-(5-Fluoro-1H-indol-2-yl)-oxazol-4-ylmethyl]-[4-(4-[1,2,3]triazol-1-yl-butyl)-phenyl]-amine;
   [2-(6-Chloro-1H-indol-2-yl)-oxazol-4-ylmethyl]-[4-(4-[1,2,3]triazol-1-yl-butyl)-phenyl]-amine
   [2-(5-Chloro-1H-indol-2-yl)-oxazol-4-ylmethyl]-[4-(4-[1,2,3]triazol-1-yl-butyl)-phenyl]-amine;
   [2-(5-Fluoro-1H-indol-2-yl)-oxazol-4-ylmethyl]-[3-methyl-4-(4-[1,2,3]triazol-1-yl-butyl)-phenyl]-amine;
   [2-(6-Fluoro-1H-indol-2-yl)-oxazol-4-ylmethyl]-[3-methyl-4-(4-[1,2,3]triazol-1-yl-butyl)-phenyl]-amine; and
   [2-(5-Chloro-1H-indol-2-yl)-oxazol-4-ylmethyl]-[3-methyl-4-(4-[1,2,3]triazol-1-yl-butyl)-phenyl]-amine.

9. A compound according to claim 1 selected from the group consisting of:
   [2-(5-Chloro-1H-indol-2-yl)-oxazol-4-ylmethyl]-[4-(4-[1,2,3]triazol-1-yl-butyl)-3-trifluoromethyl-phenyl]-amine;
   [2-(5-Fluoro-1H-indol-2-yl)-oxazol-4-ylmethyl]-[4-(4-[1,2,3]triazol-1-yl-butyl)-3-trifluoromethyl-phenyl]-amine;
   [2-(5-Fluoro-1H-indol-2-yl)-oxazol-4-ylmethyl]-[3-fluoro-4-(4-[1,2,3]triazol-1-yl-butyl)-phenyl]-amine;
   [2-(5-Chloro-1H-indol-2-yl)-oxazol-4-ylmethyl]-[3-fluoro-4-(4-[1,2,3]triazol-1-yl-butyl)-phenyl]-amine;
   [2-(5-Fluoro-1H-indol-2-yl)-oxazol-4-ylmethyl]-[2-fluoro-4-(4-[1,2,3]triazol-1-yl-butyl)-phenyl]-amine;
   [2-(5-Chloro-1H-indol-2-yl)-oxazol-4-ylmethyl]-[2-fluoro-4-(4-[1,2,3]triazol-1-yl-butyl)-phenyl]-amine;
   [2-(6-Chloro-1H-indol-2-yl)-oxazol-4-ylmethyl]-[3-(3-[1,2,3]triazol-1-yl-propyl)-phenyl]-amine;
   [2-(5-Fluoro-1H-indol-2-yl)-oxazol-4-ylmethyl]-[3-(3-[1,2,3]triazol-1-yl-propyl)-phenyl]-amine;
   [2-(5-Fluoro-1H-indol-2-yl)-oxazol-4-ylmethyl]-[6-(4-[1,2,3]triazol-1-yl-butyl)-pyridin-3-yl]-amine;
   [2-(5-Fluoro-1H-indol-2-yl)-oxazol-4-ylmethyl]-[5-(4-[1,2,3]triazol-1-yl-butyl)-pyridin-2-yl]-amine;
   5-Fluoro-2-{4-[3-methyl-4-(2-[1,2,3]triazol-1-yl-ethoxymethyl)-phenoxymethyl]-oxazol-2-yl}-1H-indole;
   5-Fluoro-2-{4-[3-methyl-4-(2-[1,2,3]triazol-1-yl-ethanesulfinylmethyl)-phenoxymethyl]-oxazol-2-yl}-1H-indole; and
   5-Fluoro-2-{4-[3-methyl-4-(2-[1,2,3]triazol-1-yl-ethanesulfonylmethyl)-phenoxymethyl]-oxazol-2-yl}-1H-indole.

10. A process for the manufacture of the compounds of formula I in claim 1, wherein:
   (a) the compound of formula VI:

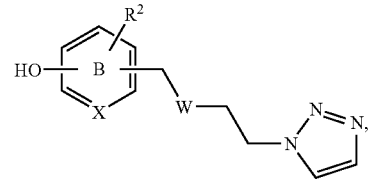

formula VI wherein R$^2$, W, X and ring B are defined according to claim 1, is (b) reacted with a compound of formula V:

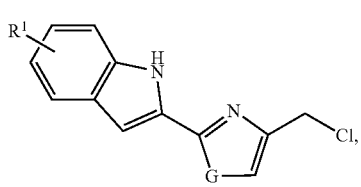

formula V wherein R¹ and G have are defined according to claim 1,
to give the respective compound of formula Ia:

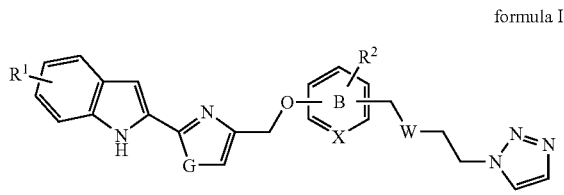

formula Ia wherein R¹, R², W, X, G and ring B are defined according to claim 1.

11. A process according to claim 10, further comprising the step of isolating the compound of formula Ia from the reaction mixture.

12. A process according to claim 10, further comprising the step of converting the compound of formula Ia into a pharmaceutically acceptable salt.

13. A process for the manufacture of the compounds of formula I in claim 1, wherein:
(a) the compound of formula XIII:

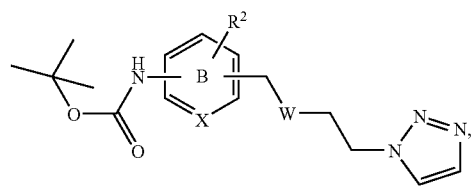

formula XIII wherein R², W, X and ring B are defined according to claim 1, is (b) reacted first with a compound of formula V:

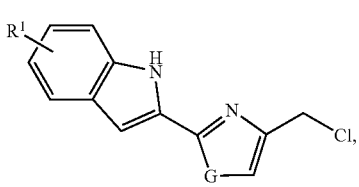

formula V wherein R¹ and G are defined according to claim 1, to give the respective compound of formula XIV:

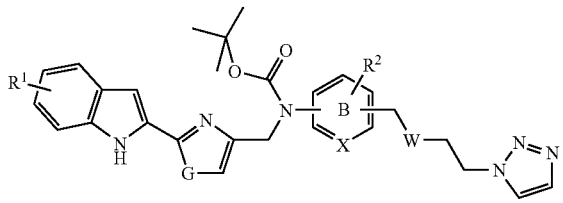

formula XIV wherein R¹, R², W, X, G and ring B are defined according to claim 1,
(c) the tert-butyloxycarbonyl(BOC)-protecting group of said compound of formula XIV is cleaved to give the respective compound of formula Ib:

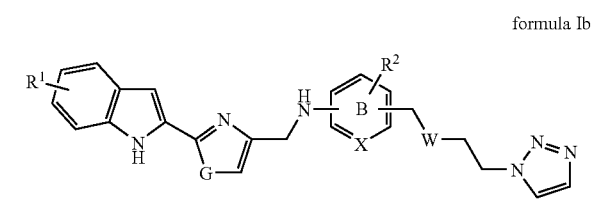

formula Ib wherein R¹, R², W, X, G and ring B are defined according to claim 1.

14. A process according to claim 13, further comprising the step of isolating the compound of formula Ib from the reaction mixture.

15. A process according to claim 13, further comprising the step of converting the compound of formula Ib into a pharmaceutically acceptable salt.

16. A pharmaceutical composition comprising a therapeutically effective amount of a compound of claim 1 and a pharmaceutically acceptable carrier.

* * * * *